US00RE46698E

(19) United States
(12) Reissued Patent
Rudolph et al.

(10) Patent Number: US RE46,698 E
(45) Date of Reissued Patent: Feb. 6, 2018

(54) USE OF CYCLOHEXANOL DERIVATIVES AS ANTIMICROBIAL ACTIVE COMPOUNDS

(71) Applicant: MERCK PATENT GMBH, Darmstadt (DE)

(72) Inventors: Thomas Rudolph, Darmstadt (DE); Tatjana Best, Hergershausen (DE)

(73) Assignee: MERCK PATENT GMBH, Darmstadt (DE)

(21) Appl. No.: 15/449,149

(22) Filed: Mar. 3, 2017

Related U.S. Patent Documents

Reissue of:
(64) Patent No.: 9,492,364
Issued: Nov. 15, 2016
Appl. No.: 14/367,530
PCT Filed: Dec. 3, 2012
PCT No.: PCT/EP2012/004980
§ 371 (c)(1),
(2) Date: Jun. 20, 2014
PCT Pub. No.: WO2013/091775
PCT Pub. Date: Jun. 27, 2013

(30) Foreign Application Priority Data

Dec. 21, 2011 (EP) ..... 11010039
Jul. 31, 2012 (EP) ..... 12005577

(51) Int. Cl.

| | |
|---|---|
| ***A01N 37/36*** | (2006.01) |
| ***A23L 3/3508*** | (2006.01) |
| ***A61K 31/215*** | (2006.01) |
| ***A61Q 11/00*** | (2006.01) |
| ***A61Q 15/00*** | (2006.01) |
| ***A61Q 19/10*** | (2006.01) |
| ***C07C 233/58*** | (2006.01) |
| ***C07C 67/303*** | (2006.01) |
| ***C07C 69/757*** | (2006.01) |
| ***C11D 3/32*** | (2006.01) |
| ***A61K 8/37*** | (2006.01) |
| ***A61K 8/42*** | (2006.01) |
| ***A61Q 17/00*** | (2006.01) |
| ***C09B 69/00*** | (2006.01) |
| ***C11D 3/20*** | (2006.01) |
| ***A61Q 5/00*** | (2006.01) |
| ***C07C 69/675*** | (2006.01) |
| ***A23L 3/3517*** | (2006.01) |
| ***C11D 3/48*** | (2006.01) |
| *A61Q 11/02* | (2006.01) |
| *A61Q 19/00* | (2006.01) |

(52) U.S. Cl.
CPC ..... *A61K 8/37* (2013.01); *A01N 37/36* (2013.01); *A23L 3/3508* (2013.01); *A23L 3/3517* (2013.01); *A61K 8/42* (2013.01); *A61K 31/215* (2013.01); *A61Q 5/006* (2013.01); *A61Q 15/00* (2013.01); *A61Q 17/005* (2013.01); *C07C 67/303* (2013.01); *C07C 69/675* (2013.01); *C07C 69/757* (2013.01); *C07C 233/58* (2013.01); *C09B 69/008* (2013.01); *C11D 3/2093* (2013.01); *C11D 3/32* (2013.01); *C11D 3/48* (2013.01); *A61K 2800/10* (2013.01); *A61K 2800/524* (2013.01); *A61K 2800/74* (2013.01); *A61Q 11/02* (2013.01); *A61Q 19/008* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 3,535,367 | A | 10/1970 | Inoue | |
| 4,228,304 | A | 10/1980 | Noda et al. | |
| 5,411,989 | A | 5/1995 | Michel et al. | |
| 5,614,486 | A | 3/1997 | Giersch et al. | |
| 5,858,958 | A | 1/1999 | Holzner | |
| 5,942,520 | A | 8/1999 | Pamukcu et al. | |
| 7,811,469 | B2 | 10/2010 | Takeuchi et al. | |
| 8,871,861 | B2 | 10/2014 | Shoshi | |
| 9,181,161 | B2 * | 11/2015 | Rudolph | A01N 31/04 |
| 2003/0199558 | A1 | 10/2003 | Dooley et al. | |
| 2004/0220137 | A1 | 11/2004 | Sauermann | |
| 2009/0268143 | A1 | 10/2009 | Takeuchi | |
| 2012/0172632 | A1 | 7/2012 | Marie et al. | |
| 2012/0321571 | A1 * | 12/2012 | Edelson | A61K 9/0014 424/59 |

FOREIGN PATENT DOCUMENTS

| | | | | |
|---|---|---|---|---|
| DE | 10133202 | A1 | 1/2003 | |
| EP | 0694605 | A2 | 1/1996 | |
| EP | 0819380 | * | 2/1997 | A01N 37/40 |
| GB | 286201 | A | 10/1929 | |
| GB | 1593469 | A | 7/1981 | |

(Continued)

OTHER PUBLICATIONS

English Translation of Office Action in corresponding Japanese Patent Application No. 2014-547737 dated Nov. 8, 2016.

Gassman et al. , π-route to azabicyclics III. The solvolysis of protonated N-chloramines: Tetrahedron Letters, 1970, 11 (54), pp. 4749-4752.

Inoki, Satoshi et al. Bis(trifluoroacetylacetonato)cobalt(II) Catalyzed Oxidation-Reduction Hydration of Olefins Selective Formation of Alcohols from Olefins; Chemistry Letters, 1989, (3), pp. 515-518.

(Continued)

*Primary Examiner* — Jerry D Johnson
(74) *Attorney, Agent, or Firm* — Millen White Zelano & Branigan, PC

(57) ABSTRACT

The present invention relates to the use of at least one cyclohexanol derivative of the formula (I) and/or (II) as antimicrobial active compound or as anti-acne, antidandruff, antiperspirant or deodorant active compound, to preparations comprising these compounds, and to specific cyclohexanol derivatives and to a process for the preparation thereof.

20 Claims, No Drawings

(56) References Cited

FOREIGN PATENT DOCUMENTS

| | | | |
|---|---|---|---|
| JP | S48-32102 | B | 10/1973 |
| JP | 5504353 | A | 7/1993 |
| JP | 2007055947 | A1 | 3/2007 |
| JP | 2007091612 | A | 4/2007 |
| JP | 2009265317 | A | 11/2009 |
| JP | 04832102 | B2 | 12/2011 |
| JP | 2013166908 | A | 8/2013 |
| RU | 2247710 | C2 | 12/2003 |
| WO | WO 91/09589 | A2 | 7/1991 |
| WO | 91/12230 | A1 | 5/1995 |
| WO | 01/42251 | A1 | 6/2001 |
| WO | 03/057184 | A2 | 7/2003 |
| WO | 2007063974 | A1 | 6/2007 |
| WO | 2011/001041 | A1 | 1/2011 |
| WO | 2011/050871 | A1 | 5/2011 |
| WO | 2011123693 | A1 | 10/2011 |

OTHER PUBLICATIONS

Lang, Lixin et al. Development of Fluorine-18-Labeled 5-HT1A Antagonists; Journal of Medicinal Chemistry, 1999, 42 (9), pp. 1576-1586.

Lang, Lixin et al. Synthesis and in vivo biodistribution of F-18 labeled 3-cis-, 3-trans-, 4-cis-, and 4-trans-fluorocyclohexane derivatives of WAY 100635; Bioorganic & Medicinal Chemistry, 2006, 14 (11), pp. 3737-3748.

Kim, In-hae et al. Structure-Activity Relationships of Cycloalkylamide Derivatives as Inhibitors of the Soluble Epoxide Hydrolase; Journal of Medicinal Chemistry, 2011, 54(6), pp. 1752-1761.

Hegazi, Ahmed et al. Egyptian Propolis: 1-Antimicrobial Activity and Chemical Composition of Upper Egypt Propolis; Zeitschrift fuer Naturforschung, C: Journal of Biosciences, 2001, 56(1/2), pp. 82-88.

Broberg, Anders et al. Metabolite Profiles of Lactic Acid Bacteria in Grass Silage; Applied and Environmental Microbiology. 2007, 73(17), pp. 5547-5552.

Registry [STN online]. entered STN on Jun. 29, 2007, RN: 940098-98-5.

Machine translation of JP2007091612A published on Apr. 12, 2007 to Fujifilm Corp.

Machine translation of JP2007055947A published on Mar. 8, 2007 to Daiichi Seimou Co Ltd.

Translation of Russian Office Action corresponding to Appln. No. 2014 129 611, dated Nov. 2, 2016.

Office Action in co-pending U.S. Appl. No. 15/215,962 dated May 19, 2017.

Machine translation of WO2007063974A1 published Jun. 7, 2007 to Sajiki Hironao of Inst Nagoya Ind Science Res.

Machine translation of JP04832102B2 published Dec. 7, 2011 to Ricoh KK.

Office Action in corresponding JP 2014-547737 dated Jun. 13, 2017.

English machine translation of WO2011050871A1 dated May 5, 2011 to Thiesen Kathrin of Beiersdorf AG.

Hagazi et al. (Proc. 37th Int. Apic. Congr., Oct. 28-Nov. 1, 2001; 7 pages).*

Okpalugo et al. (Tropical Journal of Pharmaceutical Research 2009, 8(1):71-77).*

Dax, S.L. (Antibacterial Chemotherapeutic Agents 2012; Springer Science & Business Media 2 pages).*

International Search Report dated Nov. 4, 2013 issued in corresponding PCT/EP2012/004980 application (pp. 1-3).

M.L. Schlossman, "Treated Pigments—New Ways to Impact Color on the Skin", Cosmetics and Toiletries, vol. 105 (Feb. 1990) pp. 53-64.

C.A. Rice-Evans et al. "Antioxidant Properties of Phenolic Compounds", Trends in Plant Science, vol. 2, No. 4 (Apr. 1997) pp. 152-159.

A.G. Hegazi et al., "Egyptian Propolis: 1-Antimicrobial Activity and Chemical Composition of Upper Egypt Propolis", Proceedings of the 37th International Apicultural Congress (Oct. 28-Nov. 1, 2001) Durban, South Africa—XP-002714338 pp. 1-8.

V.L. Gein et al., "Synthesis and Antimicrobial Activity of 2-Acetyl-5-Hydroxy-Methyl-3-Phenyl-1-Cyclohexanone and Alkyl-4-Hydroxy-Methyl-2-Oxo-6-Phenylcyclohexane-1-Carboxylates", Pharmaceutical Chemistry Journal, vol. 44, No. 5 (2010) pp. 245-247.

Database Registry [Online] Chemical Abstracts Service "Cyclohexanecarboxylic Acid, 3-Hydroxy-Phenylmethyl Ester", XP002714340 (Nov. 17, 1989).

Database Registry [Online] Chemical Abstracts Service "Cyclohexanecarboxylic, 4-Hydroxy-, Ethyl Ester", XP002714341 (Nov. 16, 1984).

* cited by examiner

USE OF CYCLOHEXANOL DERIVATIVES AS ANTIMICROBIAL ACTIVE COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present invention relates to the use of at least one cyclohexanol derivative of the formula I and/or II as antimicrobial active compound or as anti-acne, antidandruff, antiperspirant or deodorant active compound, to preparations comprising these compounds, and to specific cyclohexanol derivatives and to a process for the preparation thereof.

Microbial contamination represents a significant problem in our daily life, for example in connection with cosmetic or pharmaceutical products, foods, surfaces in bathrooms or kitchens or surgical instruments. Use is usually made of preservatives in order to prevent microbial contamination. However, antimicrobial active compounds are not only necessary as preservatives. Antimicrobial active compounds also play an important role for many cosmetic uses:

Dandruff formation is a disorder of the scalp which is widespread in the population and is usually accompanied by mild to moderate itching. The formation of usual dandruff of this type should not be regarded as a skin disease in the general sense. Dandruff may arise due to scalp disorders, which may be triggered, for example, by excessive exposure to the sun, environmental influences from the air or cosmetic hair products. The dandruff is in this case formed by excessive production of keratinocytes, triggered by tiny centres of inflammation of the scalp, whose cause is, for example, increased microbial colonisation by fungi (such as Malassezia furfur or Malassezia globosa) or bacteria. The incompletely matured keratinocytes consequently flake off prematurely in relatively large cell clusters (dandruff). Since the outermost skin layer becomes thinner due to the loss of skin cells, dandruff formation results in increased sensitivity of the scalp, which is evident in itching and reddening.

Acne is taken to mean a skin disorder which is evident in inflamed papules, pustules or nodules, caused by increased talc production and impaired keratinisation of the skin. The inflammation may be associated with reddening, swelling and pressure pain. Besides genetic predisposition, possible causes of acne formation can be androgens, comedogenic substances (for example in cosmetics), smoking, stress or excessive colonisation of the skin by bacteria. Acne can be triggered, for example, by microorganisms, such as Propionibacterium acnes, Propionibacterium granulosum or Staphylococcus epidermidis. Propionibacterium acnes is a bacterium which usually colonises the skin and lives on sebum. Acne may arise, for example, if the number of these bacteria is increased. The presence of bacteria in the follicles results in inflammation reactions, which is evident in the form of red nodules or pustules. The production of free fatty acids by the bacteria furthermore promotes the inflammation reaction in the follicle.

Besides water and salt, axillary sweat contains many other substances (such as fats, amino acids, sugars, lactic acid, urea, etc.). Freshly formed sweat is odourless; the typical sweat odour only forms due to the action of skin bacteria on the sweat, which decompose the latter. Examples of such bacteria are Staphylococcus, Corynebacterium or Malassezia. For this reason, antimicrobial substances are usually also employed besides aroma substances and antiperspirants in deodorants and antiperspirants, with the aim of controlling the bacteria which are involved in the odour formation.

In the case of the use of antimicrobial substances in preparations, their compatibility in particular, but also their formulatability (i.e. solubility, stability, etc.) in the corresponding products (for example shampoos, creams, deodorants) is of major importance. In particular in cosmetics, these properties are essential. Thus, for example, it is particularly desirable for the ingredients to be in the liquid physical state at atmospheric pressure between −5° C. and 40° C.

The aim of the present invention is therefore the provision of novel ingredients having an antimicrobial action which have the above-mentioned advantageous properties.

Surprisingly, it has now been found that certain cyclohexanol derivatives have the above-mentioned properties at the same time as an excellent antimicrobial action.

Similar compounds for use in cosmetics are described in the prior art:

U.S. Pat. No. 5,858,958 describes 4-t-butylcyclohexanol as effective antioxidant. An antimicrobial action is not described.

Phosphoric acid esters of cycloalkanecarboxylic acids for use in oral and dental care compositions are disclosed in WO 91/09589.

WO 03/057184 A2 describes the use of benzohydroxamides for lightening the skin.

A further known cyclohexanol derivative is p-menthane-3,8-diol (PMD), which, as constituent of the ethereal oil of lemon eucalyptus, has an insect-repellent action.

The present invention therefore relates firstly to the use of at least one compound of the formula I and/or II

I

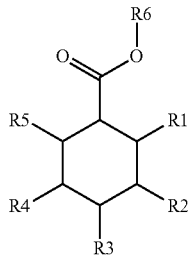

II

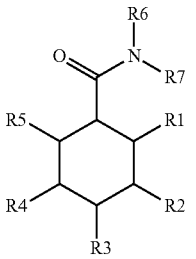

in which R1, R2, R3, R4 and R5 stand, independently of one another, for a radical selected from H, OH, $OCOCH_3$, $O—(CH_2—CH_2—O)_n—CH_2—CH_2—OH$, where n=0 to 20, straight-chain or branched alkyl or alkoxy group having 1 to 20 C atoms, where at least one of the radicals R1, R2, R3, R4 and R5 stands for OH, $OCOCH_3$ or $O—(CH_2—CH_2—O)_n—CH_2—CH_2—OH$, where n=0 to 20, and in which R6 and R7 stand, independently of one another, for a radical selected from

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, where the alkyl, alkenyl or alkynyl group may also contain one or more saturated or unsaturated $C_3$- to $C_{12}$-cycloalkyl groups, as antimicrobial active compound.

An antimicrobial active compound is in accordance with the invention taken to mean a substance which reduces the growth of microorganisms or destroys or deactivates the microorganisms.

The compounds of the formula I and/or II according to the invention can be used in order to inhibit the growth and reproduction of microorganisms. Microorganisms are taken to mean, for example, bacteria (Gram-positive and Gram-negative bacteria), yeasts, fungi or viruses. Examples of microorganisms are microorganisms selected from Staphylococcus, Micrococcus, Escherichia, Pseudomonas, Bacillus, Salmonella, Serratia, Shigella, Porphyromonas, Prevotella, Wolinella, Campylobacter, Propionibacterium, Streptococcus, Corynebacterium, Treponema, Fusobacterium, Bifidobacterium, Lactobacillus, Actinomyces, Candida, Malassezia, Aspergillus, Herpes simplex 1 and 2.

In particular, compounds according to the invention are antimicrobially active against Staphylococcus epidermidis, Staphylococcus aureus, Corynebacterium xerosis, Malassezia furfur, Propionibacterium acnes, Pseudomonas aeruginosa, Salmonella enteric, Serratia marcescens, Aspergillus niger and Candida albicans.

The antimicrobial compounds of the formula I and/or II are distinguished by good antimicrobial activity, which means that the number of microbes in a medium can be reduced reproducibly or microbe reproduction is suppressed (see examples).

The antimicrobial active compounds according to the invention can be used in a multiplicity of formulations or applications, such as, for example, cosmetic/pharmaceutical formulations, medicinal products, foods, household products, plastics, paper and/or paints. In particular, they can be, for example, antimicrobial cleaning products, soaps, disinfectants, prostheses or bone cement having an antimicrobial activity, dental fillings and prostheses, dental and oral care products, body care products (creams, shampoos, lotions, washing products, deodorants, antiperspirants, antimicrobial hand-washes, etc.), hygiene articles, kitchen and bathroom articles, dishwashing products or foods and drinks.

The compounds of the formula I and/or II can advantageously be employed for improving preservation.

The antimicrobial active compounds according to the invention are advantageously used, for example, in dental or oral care products, for example for the treatment or prophylaxis of plaque, caries or bad breath, triggered by microorganisms such as Streptococcus sobrinus, Streptococcus mutans, Streptococcus gordonii, Streptococcus salivaris, Streptococcus sanguis, Actinomyces, Lactobacilli, Fusobacterium, Veillonella, Treponema. denticola, Porphyromonas. gingivalis, Bacteroides or Peptostreptococcus.

As multifunctional substances, the compounds of the formula I and/or II are suitable for use as antioxidants or fragrant aroma substances for the deodorisation and masking of undesired inherent odours of the ingredients in formulations. In particular, a combination with further antioxidants and fragrances is conceivable in this respect. This encompasses, for example, all fragrances as described in "S. Arctander, Perfume and Flavor Materials, Vol. I and II, Montclair, N.J., 1969, Selbstverlag" or in "K. Bauer, D. Garbe and H. Surburg, Common Fragrance and Flavor Materials, 4th Ed., Wiley-VCH, Weinheim 2001" or as described in U.S. Pat. No. 7,354,893 B2, in particular described in U.S. Pat. No. 7,354,893, column 2, lines 37 to 67.

Owing to their material properties, substances according to the invention are highly suitable for incorporation into emulsions and surfactant preparations, such as, for example, detergents and so-called rinse-off preparations, such as, for example, shower gels. Substances according to the invention are, for example, in liquid form at room temperature and are suitable on the one hand as solvents for solids, on the other hand they exhibit emollient properties with good spreading behaviour, which causes a pleasant skin feel of the formulation.

Furthermore, substances according to the invention are suitable as skin moisturisers, in particular in synergistic combination with further skin humectants, such as, for example, glycerol, glycerol derivatives, hyaluronic acid, urea, urea derivatives, ectoin, lactic acid and lactates, collagen, AHAs. Illustrative skin humectants are described on page 27, line 4 to page 28 line 17 of WO 2009/098139.

They may furthermore have astringent, skin-cooling, antistatic or hair-conditioning properties. The compounds of the formula I and/or II are suitable as additives for skin care. This includes anti-ageing action, anti-irritation action and anti-inflammatory action. Undesired skin reddening can thus be reduced.

Substances according to the invention can furthermore be used for improving the skin barrier function, in particular in synergistic combination with further active compounds in this area, such as, for example, lanolin, shea butter, phospholipids, cholesterol and cholesterol derivatives, phytosterols, essential fatty acids, such as linoleic acid and linolenic acid, omega-3 unsaturated oils, ceramides, such as, for example, type 2 or 3 ceramides, sphigosines, such as, for example, salicyloyl sphingosine, or amino acid, such as serine or arginine. Illustrative active compounds which improve the skin barrier function are described on page 30, line 6 to page 31, line 10 of WO 2009/098139.

It is furthermore conceivable for substances according to the invention to exhibit positive effects in compositions for pigmentation control, i.e. supporting darkening or lightening of the skin colour. In the case of the use for skin lightening, combination with further skin-lightening active compounds is particularly preferred. These include, for example, vitamin C and vitamin C derivatives, such as 2-O-vitamin C glucoside, 2-O-vitamin C phosphate, 2-O—, or 3-O-ethyl vitamin C or 6-O-p-methoxycinnamoylascorbic acid, alpha and beta arbutin, ferulic acid, lucinol and lucinol derivatives, kojic acid, resorcinol and resorcinol derivatives, tranexamic acid and derivatives thereof, gentisic acid and derivatives thereof, lipoic acid, ellagic acid, vitamin B3 and vitamin B3 derivatives, extracts, such as, for example, mulberry extracts. Illustrative skin-lightening active compounds are described on page 31, line 14 to page 32, line 7 of WO 2009/098139.

Likewise conceivable are compositions for skin lightening comprising substances according to the invention in combination with substances as disclosed in WO 2007/121845, in particular the compounds of claims 12 and 13 of WO 2007/121845.

Further functional properties which the substances according to the invention may include, or which may be supported or improved by them in combination with specific active compounds, include, for example, the substances mentioned in WO 2009/098139.

In particular in combination with traditional preservatives, improvements in the preservation result can be achieved. The action of cosmetic alcohols, such as, for example, glycols, can be enhanced by the substances.

In light-protection formulations, substances according to the invention are highly suitable for increasing protection factors (sun protection factor SPF, UVA protection factors, such as PPD [persistent pigment darkening], factors which express the protection against infrared, or visible light), and also for stabilising photounstable UV filters, in particular dibenzoylmethane derivatives, such as, for example, butylmethoxydibenzoylmethane (Eusolex 9020).

Illustrative actions include antiglycation action, dermorelaxing action, activation of the skin's own macromolecules, such as, for example, activation of collagen and elastin, and protection thereof against degradation, activation of fibroblast or keratinocyte proliferation, inhibition of NO synthase, sebum-regulating action, cell energy metabolism-stimulating action, in particular in combination with salts of manganese, zinc, copper, magnesium and beta-glucan, skin-tightening action, anticellulite action, in particular in combination with xanthines, such as, for example, caffeine, fat-restructuring action, such as, for example, lipolytic action (slimming action), anti-inflammatory action, for example in combination with hydrocortisone and folic acid or derivatives thereof, It is furthermore conceivable for substances according to the invention to counter skin ageing, including light-induced skin ageing, in a preventative manner by inhibiting, for example, matrix metalloproteinases (MMPs) or contributing to DNA protection. In a further application, the substances contribute to wound healing.

The present invention furthermore relates to the use of the compounds of the formula I and/or II as anti-acne, antidandruff, antiperspirant or deodorant active compound.

In particular, the compounds of the formula I and/or II are suitable for the treatment or prophylaxis of acne which is triggered by microorganisms, such as Propionibacterium acnes, Propionibacterium granulosum or Staphylococcus epidermidis.

Suitable formulations for this purpose are described below.

Furthermore, the use of compounds of the formula I and/or II as antidandruff active compound is advantageous, both for treatment and also for prophylaxis. Suitable formulations, for example shampoos, are described below.

Also advantageous is the use as active compound in antiperspirants or deodorants. On the one hand, some of the compounds according to the invention have a pleasant inherent odour which can mask unpleasant odours and thus have a deodorant action. For example, compound 1-2 smells of apple, while compound I-20 smells of raspberry (definitions of the compounds see below).

The use in deodorants and antiperspirants is furthermore advantageous since the compounds of the formula I and/or II have an antimicrobial action against the bacteria which are responsible for the decomposition of sweat and thus for the formation of the odour. It is particularly advantageous here that the compounds can have a bacteriostatic or bactericidal action depending on the test microbe. A bacteriostatic action is achieved if the reproduction of a bacterium is inhibited, suppressing the formation of an odour, but the bacterium is not killed. The natural skin flora can thereby advantageously be maintained.

Thus, for example, the compounds of the formula I-2, I-9 and I-10 have a bacteriostatic action against Staphylococcus epidermidis, while the action of the compound of the formula I-20 on S. epidermidis is bactericidal (Example 5).

Possible formulations for deodorants and antiperspirants are described below.

The use according to the invention of the compounds of the general formula I and/or II can take place both in the cosmetic sense and also in the pharmaceutical sense. A pharmaceutical application is conceivable, for example, in the case of anti-acne compositions.

The use is preferably cosmetic. Thus, a non-therapeutic use of the above-mentioned compounds or preparations thereof for the prevention of undesired changes in the skin picture, as occurs in the case of acne, is possible.

The compounds of the formula I and II have an unexpectedly good antimicrobial action, as explained in the examples. Furthermore, the compounds of the formula I and II can advantageously be used in formulations, since they are clear liquids which can be incorporated well into the corresponding formulations.

In accordance with the invention, the compounds of the formulae I and/or II encompass all possible ring configuration isomers, i.e. both cis, and also trans isomers are conceivable.

It is likewise known for the person skilled in the art that the atoms of the compounds can also be replaced by other isotopes, thus, for example, replacement of the H atoms by D is possible.

A compound of the formula I is preferably used.

In a preferred embodiment, the radicals R1, R2, R3, R4 and R5 stand, independently of one another, for H or OH, where 1, 2 or 3 of the radicals R1, R2, R3, R4 and R5 stand for OH.

Examples of such compounds are listed below:

I-1

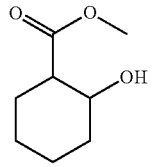

I-2

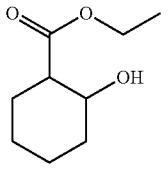

I-3

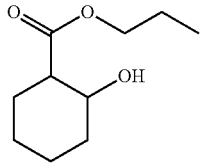

-continued
I-4
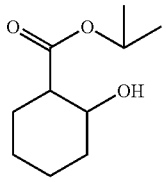
I-5
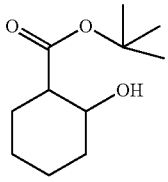
I-6
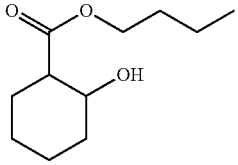
I-7
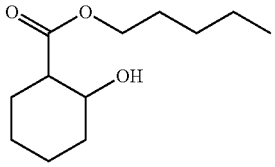
I-8
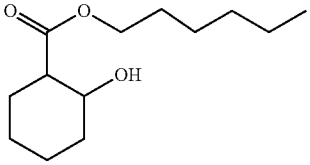
I-9
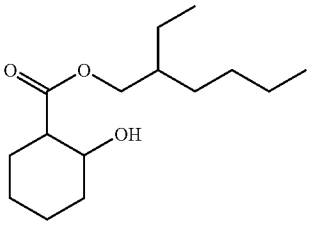
I-10
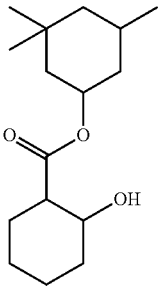
I-11
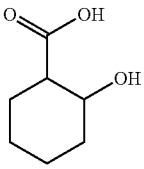
-continued
I-12
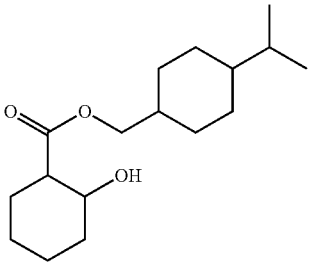
I-13
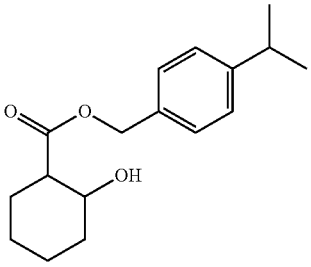
I-14
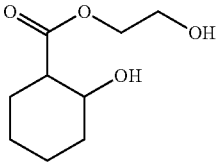
I-15
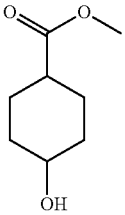
I-16
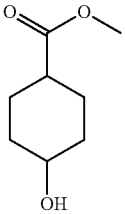
I-17
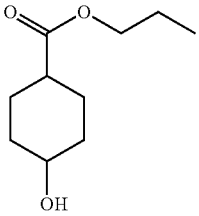
I-18
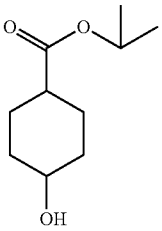

-continued
I-19
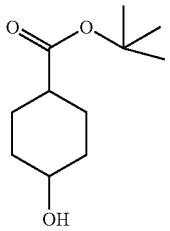
I-20
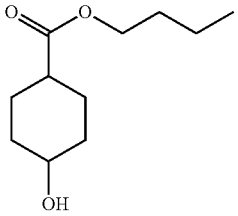
I-21
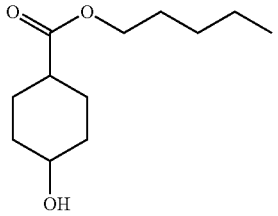
I-22
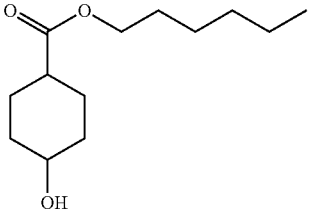
I-23
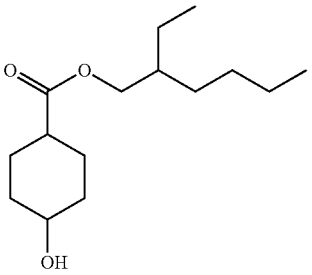
I-24
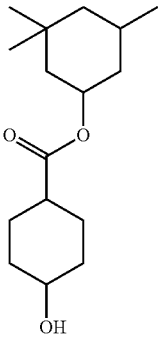
-continued
I-25
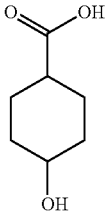
I-26
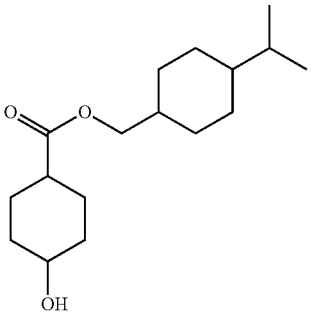
I-27
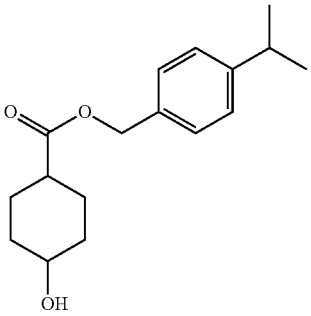
I-28
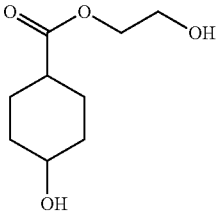
I-29
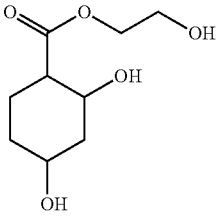
I-30
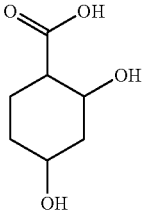

-continued

I-31

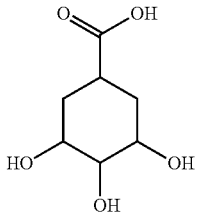

I-32

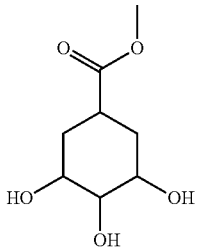

I-33

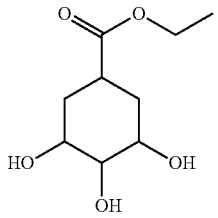

I-34

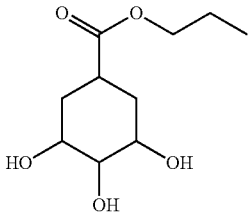

I-35

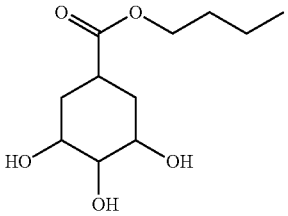

Examples of compounds containing other radicals R1, R2, R3, R4 and R5 are:

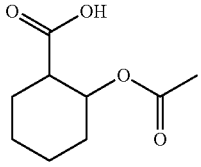

,

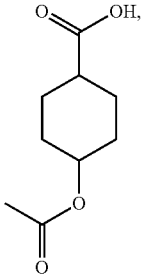

,

-continued

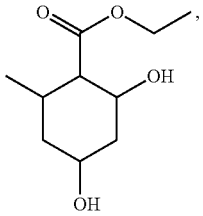

,

Furthermore preferably, precisely one of the radicals R1, R2, R3, R4 and R5 stands for OH, while the other radicals stand for H. Particularly preferably, the OH group is then located in the p- or m-position, i.e. particularly preferably in this case one of the radicals R1, R3 and R5 stands for OH.

For the use according to the invention, preference is therefore given to compounds of the formula I and II, selected from the compounds of the formula Ia, Ib, IIa and IIb Ia

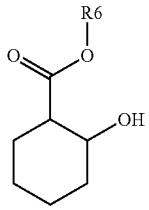

Ib

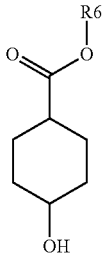

IIa

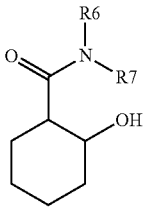

IIb

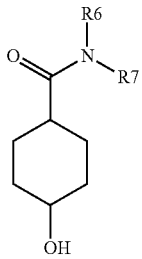

in which R6 and R7 stand, independently of one another, for a radical selected from

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, where the alkyl, alkenyl or alkynyl group may also contain one or more saturated or unsaturated $C_3$- to $C_{12}$-cycloalkyl groups.

Preference is given to the compounds of the formula Ia and Ib.

The radicals R6 and R7 in the definitions above preferably stand, independently of one another, for a radical selected from

H, $CH_2$—$CH_2$—OH, straight-chain or branched alkyl group having 1 to 10 C atoms, which may also contain a saturated or unsaturated $C_6$-cycloalkyl group.

Particular preference is given in accordance with the invention to the use of a compound of the formula I, selected from the compounds of the formula I-1 to I-28

I-1

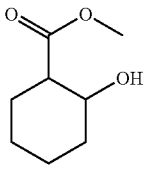

I-2

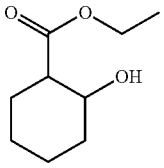

I-3

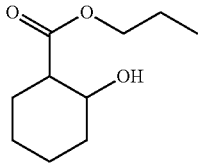

I-4

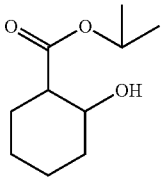

I-5

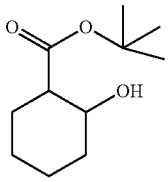

I-6

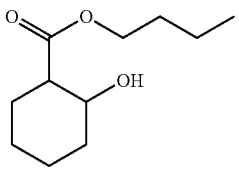

-continued

I-7

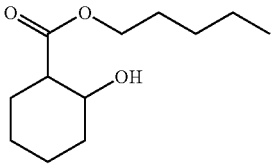

I-8

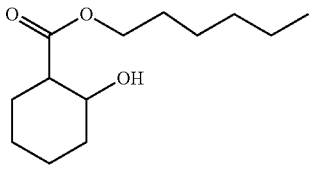

I-9

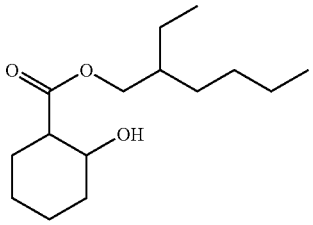

I-10

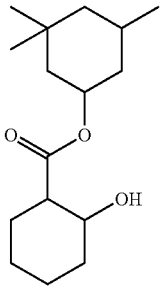

I-11

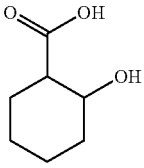

I-12

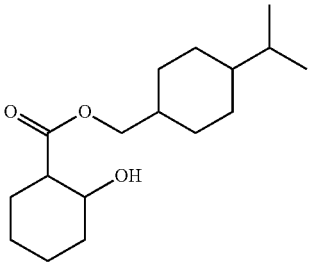

I-13

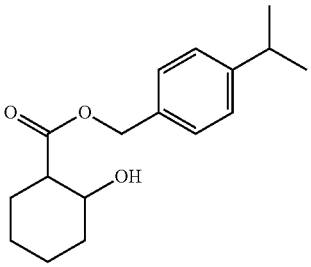

-continued
I-14
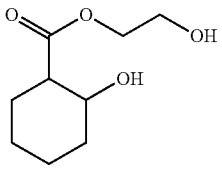
I-15
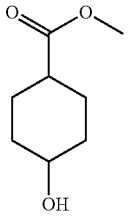
I-16
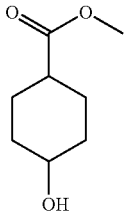
I-17
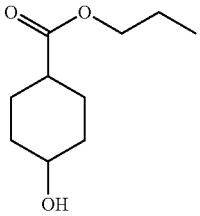
I-18
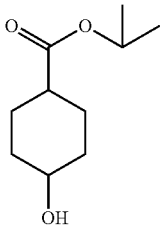
I-19
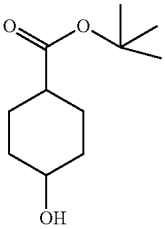
I-20
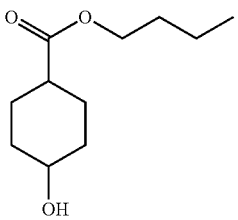
-continued
I-21
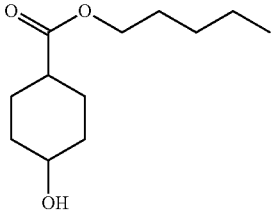
I-22
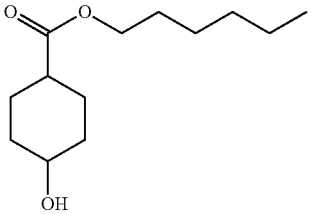
I-23
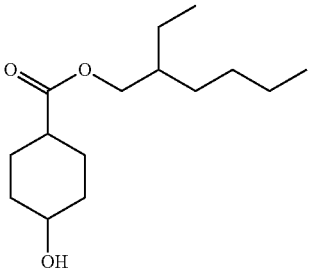
I-24
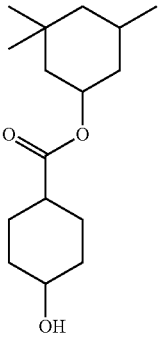
I-25
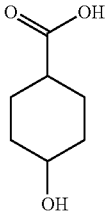
I-26
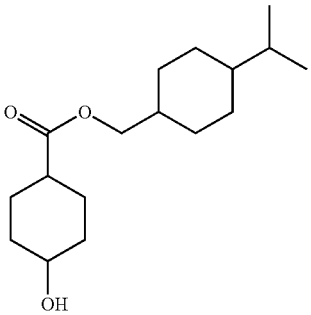

-continued

I-27

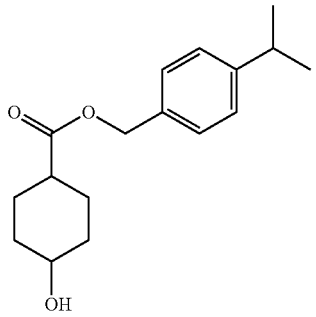

I-28

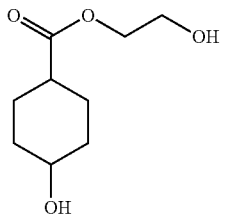

Very particular preference is given to compounds I-2, I-9 and I-10.

For the purposes of the present invention, a straight-chain or branched $C_1$- to $C_{10}$-alkyl group is an alkyl radical having 1 to 10 C atoms, for example methyl, ethyl, isopropyl, propyl, butyl, sec-butyl or tert-butyl, pentyl, isopentyl, 1-, 2- or 3-methylbutyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, 1,1-, 1,2-, 1,3-, 2,2-, 2,3- or 3,3-dimethylbutyl, 1- or 2-ethylbutyl, 1-, 2-, 3- or 4-methylpentyl, hexyl, heptyl, 1-ethylpentyl, octyl, 1-ethylhexyl, nonyl or decyl.

Besides the radicals listed above, a $C_1$- to $C_{20}$-alkyl group can also be, for example, undecyl, dodecyl, tridecyl, tetradecyl, pentadecyl, hexadecyl, heptadecyl, octadecyl, nonadecyl or eicosyl.

In accordance with the invention, an alkenyl group may contain one or more double bonds. A straight-chain or branched $C_2$- to $C_{20}$-alkenyl group is, for example, allyl, vinyl, propenyl, 2- or 3-butenyl, isobutenyl, sec-butenyl, 2-methyl-1- or 2-butenyl, 3-methyl-1-butenyl, 1,3-butadienyl, 2-methyl-1,3-butadienyl, 2,3-dimethyl-1,3-butadienyl, 1-, 2-, 3- or 4-pentenyl, iso-pentenyl, hexenyl, heptenyl or octenyl, —$C_9H_{17}$, —$C_{10}H_{19}$ to —$C_{20}H_{39}$.

An alkynyl group may contain one or more triple bonds. Examples of a branched or unbranched $C_2$- to $C_{20}$-alkynyl group are ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$.

A $C_3$- to $C_{12}$-cycloalkyl group in the sense of the invention denotes saturated and partially or fully unsaturated (i.e. also aromatic) cyclic hydrocarbon groups which contain 3 to 12 C atoms and may also be bridged by —$(CH_2)_n$ groups, where n=1, 2 or 3. The bonding to the respective radical can take place via any ring member of the cycloalkyl group. Examples of suitable cycloalkyl radicals are cyclopropyl, cyclobutyl, cyclopentyl, cyclohexyl, cycloheptyl, cyclooctyl, cyclopentenyl, cyclopentadienyl, cyclohexenyl, cyclooctadienyl or phenyl.

A cyclic alkyl radical having 6 C atoms is preferably cyclohexyl, cyclohexenyl or phenyl.

The compounds of the formula I and II can be prepared by means of hydrogenation of corresponding aromatic starting materials by methods known to the person skilled in the art using hydrogen and using a suitable Ni, Co, Pt, Pd or Rh catalyst. (see, for example, GB 286201, Example 3).

The starting materials, and the other substances necessary in the synthesis, are commercially available or accessible by syntheses which are known to the person skilled in the art from the literature. The person skilled in the art is presented with no difficulties here in selecting the suitable reaction conditions, such as solvents or temperature.

The reaction is typically carried out at temperatures below 100° C. and a pressure less than 200 bar, for example at 100 bar or 5 bar.

Examples of possible solvents are 2-propanol or tetrahydrofuran.

The reaction time is typically several hours, for example 3 to 5 hours.

Alternatively, the hydrogenation can also be carried out by means of the process described in WO 2011/001041 A1.

The present invention furthermore also relates to a preparation comprising at least one compound of the formula I and/or II, as defined above, and at least one suitable vehicle.

The preparation can be both a cosmetic preparation and a pharmaceutical preparation. It is preferably a cosmetic preparation.

Preferred embodiments of the radicals R1 to R7 of the formula I and II are defined here as described above.

The preparations here are, for example, preparations which can be applied topically, for example cosmetic or dermatological formulations or medicinal products. The preparations in this case comprise a topically cosmetically or dermatologically suitable vehicle and, depending on the desired property profile, optionally further suitable ingredients. In the case of pharmaceutical preparations, the preparations in this case comprise a pharmaceutically tolerated vehicle and optionally further pharmaceutical active compounds. Preparations for use in the mouth comprise a vehicle which is suitable for these applications.

In the sense of the present invention, the term composition or formulation is also used synonymously alongside the term preparation.

Can be applied topically in the sense of the invention means that the preparation is used externally including the oral cavity and locally, i.e. that the preparation must be suitable for application, for example, to the skin.

The preparations may include or comprise, essentially consist of or consist of the said requisite or optional constituents. All compounds or components which can be used in the preparations are either known and commercially available or can be synthesised by known processes.

The at least one compound of the formula I and/or II is typically employed in the preparations according to the invention in amounts of 0.01 to 20% by weight, preferably in amounts of 0.05 to 10% by weight, particularly preferably in amounts of 0.1% by weight to 5% by weight and very particularly preferably in amounts of 0.5 to 2% by weight, based on the total amount of the preparation. The person skilled in the art is presented with absolutely no difficulties here in selecting the amounts correspondingly depending on the intended action of the preparation.

The preparation is preferably a deodorant, an antiperspirant, an antidandruff or anti-acne composition or an antibacterial preparation, in particular for dental or oral care.

Anti-acne compositions comprising the compounds according to the invention can be in the form of soaps, cleansers, solutions, suspensions, emulsions, creams, gels, pastes, lotions, powders, oils, sticks or sprays. Further possible ingredients in the formulations are described in detail below.

Antidandruff compositions comprising the compounds according to the invention can be, for example, in the form of a shampoo or rinse which can be applied to the hair before or after washing, colouring or bleaching. Alternatively, a formulation is also possible in the form of a lotion or gel for hair styling, for hair treatment or for hair drying, in the form of a hair lacquer, a formulation for permanent wave, or a formulation for hair colouring or bleaching. A cosmetic formulation of this type may comprise a number of further ingredients, such as surface-active substances, thickeners, polymers, softeners, preservatives, foam stabilisers, electrolytes, organic solvents, silicone derivatives, antigrease active compounds, dyes or pigments which colour the formulation or the hair, or other ingredients which are usually used in hair care products. Further ingredients are described in detail below in the application.

Deodorants and antiperspirants can be, for example, in the form of creams, gels, lotions, emulsions, deodorant sticks, rollers, sprays or pump sprays. The compounds of the formula I and/or II are usually combined with vehicle materials, ingredients and active compounds which are suitable for deodorants and antiperspirants. Mention may be made here by way of example of combinations with all vehicle materials, ingredients and active compounds mentioned in WO 2011/131474. Combinations with further deodorant adjuvants are regarded as particularly preferred, such as, for example, from the groups of the silver salts and/or silver complexes and/or minerals of volcanic origin and/or zeolites and/or alum and/or hair-growth-inhibiting substances. Illustrative silver salts and/or silver complexes are described on page 6, line 7 to page 10, line 14 of WO 2011/131474. Minerals of volcanic origin are described by way of example on page 10, line 15 to page 11, line 5 of WO 2011/131474. Zeolites are described by way of example on page 11, line 7 to line 27 of WO 2011/131474. Salts of the alum type are described by way of example on page 11, line 28 to page 13, line 17 of WO 2011/131474. Illustrative hair-growth-inhibiting substances are described on page 13, line 29 to page 21, line 11 of WO 2011/131474.

Examples of suitable vehicle materials are glyceryl stearate, aluminium chlorohydrate, propylene glycol, carbomer, glycerol, dicapryl ether, ethanol, glyceryl cocoate, cyclomethicone, dimethicone, dipropylene glycol, stearyl alcohol, mineral oil, phenyltrimethicone or sodium stearate.

In the above-mentioned formulations, the compounds of the formula I and/or II can advantageously be combined with all further known preservatives or antimicrobial active compounds, such as, for example, anisic acid, alcohol, ammonium benzoate, ammonium propionate, benzoic acid, bronopol, butylparaben, benzethonium chloride, benzalkonium chloride, 5-bromo-5-nitro-1,3-dioxane, benzyl alcohol, boric acid, benzisothiazolinone, benzotriazole, benzyl hemiformate, benzylparaben, 2-bromo-2-nitropropane-1,3-diol, butyl benzoate, chlorphenesin, capryl/capric glycerides, caprylyl glycol, Camellia Sinensis leaf extract, Candida Bombicola/glucose/methyl rapeseedates, chloroxylenol, chloroacetamide, chlorhexidine, chlorobutanol, calcium benzoate, calcium paraben, calcium propionate, calcium salicylate, calcium sorbate, captan, chloramine T, chlorhexidine diacetate, chlorhexidine digluconate, chlorhexidine dithydrochloride, chloroacetamine, p-chloro-m-cresol, chlorphen, p-chlorophenol, chlorothymol, Citrus Grandis (grapefruit) fruit extract, Citrus Grandis (grapefruit) seed extract, m-cresol, o-cresol, p-cresol, mixed cresols, 1,2-decanediol (INCI Decylene Glycol), diazolidinylurea, dichlorobenzyl alcohol, dimethyloxazolidine, DMDM hydantoin, dimethylhydroxmethylpyrazole, dehydroacetic acid, diazolidinylurea, DEDM hydantoin, DEDM hydantoin dilaurate, dibromopropamidine diisothionate, dimethylolethylenethiourea, dithiomethylbenzamide, DMHF, domiphen bromide, 7-ethylbicyclooxazolidine, ethylparaben, ethylhexylglycerol, ethanol, ethyl ferulate, formaldehyde, ferulic acid, glyceryl caprate, glutaral, glycerol formate, glyoxal, hexamidine diisethionate, hexanediol, hexetidine, hexamidine, hexamidinediparaben, hexamidineparaben, 4-hydroxybenzoic acid, hydroxymethyldioxazabicyclooctane, imidazolidinylurea, imidiazolidinylurea NF, isobutylparaben, isothiazolinone, iodopropynylbutyl carbamate, isodecylparaben, isopropylcresol, isopropylparaben, isopropyl sorbate, potassium sorbate NF FCC, copper usnate, potassium benzoate, potassium ethylparaben, potassium methylparaben, potassium paraben, potassium phenoxide, potassium o-phenylphenate, potassium propionate, potassium propylparaben, potassium salicylate, potassium sorbate, methylparaben, methylisothiazolinone, methylbenzethonium chloride phenol, methyldibromoglutaronitrile, methenammonium chloride, methylbromoglutaronitrile, magnesium benzoate, magnesium propionate, magnesium salicylate, MDM hydantoin, MEA benzoate, MEA o-phenylphenate, MEA salicylate, methylchloristhiazolinone, sodium benzoate NF FCC, sodium caprylate, sodium dehydroacetate, sodium dehydroacetates FCC, sodium hydroxymethylglycinate, sodium methylparaben, sodium propylparaben, sodium iodoate, neem tree seed oil, nisin, sodium benzoate, sodium butylparaben, sodium p-chloro-m-cresol, sodium ethylparaben, sodium formate, sodium hydroxymethanesulfonate, sodium isobutylparaben, sodium paraben, sodium phenolsulfonate, sodium phenoxide, sodium o-phenylphenate, sodium propionate, sodium propylparaben, sodium pyrithione, sodium salicylate, sodium sorbate, ortholphenylphenol, phenoxyethanol, propylparaben, polymethoxybicyclicoxazolidine, Pinus Pinaster bark extract, poloxamer 188, PVP iodine, parabens, pircotone olamines, phenethyl alcohol, polyaminopropylbiguanide, polyquarternium-42, PEG-5 DEDM hydantoin, PEG-15 DEDM hydantoin, PEG-5 hydantoin oleate, PEG-15 DEDM hydantoin stearate, phenethyl alcohol, phenol, phenoxyethylparaben, phenoxyisopropanol, phenyl benzoate, phenyl mercury acetate, phenyl mercury benzoate, phenyl mercury borate, phenyl mercury bromide, phenyl mercury chloride, phenylparaben, o-phenylphenol, polyaminopropylbiguanide stearate, propionic acid, propyl benzoate, quaternium-15, quaternium-8, quaternium-14, Rosmarinus officinalis leaf extract, sorbic acid NF FCC, selenium disulfine, sorbic acid, salicylic acid, silver borosilicate, silver magnesium aluminium phosphate, triclosan, di-alpha-tocopherol, tocopherol acetate, thimersal, triclocarban, TEA sorbate, thimerosal, usnic acid, undecylenoyl PEG-5 paraben, Vitis vinifera seed extract, tea tree oil, hydrogen peroxide, zinc pyrithione, zinc oxide, zinc phenolsulfonate or combinations thereof.

In the above-mentioned formulations, the compounds of the formula I and/or II can advantageously be combined with one or more insect-protection agents (insect repellents). Important insect-protection agents are, for example, N,N-diethyl-m-toluamide (DEET), p-menthane-3,8-diol (PMD) or IR3535 (3-[N-butyl-N-acetyl]aminopropionic acid, ethyl ester). Substances according to the invention may also themselves have insect-repellent properties or contribute to improved defence in combination with further insect-protection agents.

The compounds of the formula I and/or II can also be combined with antibiotics. In accordance with the invention, use can be made of all known antibiotics, for example beta-lactam, vancomycin, macrolides, tetracyclines, quinolones, fluoroquinolones, nitrated compounds (such as nitroxoline, tilboquinol or nitrofurantoin), aminoglycosides, phenicols, lincosamida, synergistins, fosfomycin, fusidic acid, oxazolidinones, rifamycins, polymixyns, gramicidins, tyrocydines, glycopeptides, sulfonamides or trimethoprims.

Formulations for oral or dental care can be, for example, in the form of a tooth cream, a mouthwash, a tooth powder, a chewing gum, a pastille, a mouth spray, dental floss, dental cement or dental colour.

Corresponding formulations may comprise further conventional ingredients, such as, for example, humectants, surface-active agents, structure formers, gel formers, abrasives, fluoride sources, desensitisers, flavours, dyes, sweeteners, preservatives, antimicrobial substances or antiplaque or anti-tartar agents.

Suitable humectants for use in tooth creams are, for example, polyhydric alcohols, such as xylitol, sorbitol, glycerol, propylene glycol or polyethylene glycol. Mixtures of glycerol and sorbitol are particularly suitable. A humectant contributes to tooth-cream formulations not drying out on contact with air and the mouth feel of the cream (soft nature, flowability, sweetness) being pleasant. These humectants are typically present in the preparation in amounts of 0-85% by weight, preferably 0-60% by weight.

Suitable surface-active substances in tooth creams, mouthwashes, etc., are typically water-soluble organic compounds and may be anionic, nonionic, cationic or amphoteric. An appropriately stable surface-active substance should preferably be selected.

Anionic surface-active substances are, for example, water-soluble salts of $C_{10-18}$ alkylsulfates (for example sodium laurylsulfate), water-soluble salts of $C_{10-18}$ ethoxylated alkylsulfates, water-soluble salts of $C_{10-18}$ alkylsarcosinates, water-soluble salts of sulfonated monoglycerides of $C_{10-18}$ fatty acids (for example sodium coconut fatty acid monoglyceride sulfonate), alkylarylsulfonates (for example sodium dodecylbenzenesulfonate) and sodium salts of the coconut fatty acid amide of N-methyltaurine.

Nonionic surface-active substances which are suitable for oral care compositions are, for example, the products of the condensation of the alkylene oxide groups with aliphatic or alkylaromatic compounds, such as polyethylene oxide condensates of alkylphenols, ethylene oxide/propylene oxide copolymers (available under the name 'Pluronic'), ethylene oxide/ethylenediamine copolymers, ethylene oxide condensates of aliphatic alcohols, long-chain tertiary amine oxides, long-chain tertiary phosphine oxides, long-chain dialkyl sulfoxides and mixtures thereof. Alternatives thereto are ethoxylated sorbitan esters, which are available, for example, via ICI under the name "Tween".

Cationic surface-active agents are typically quaternary ammonium compounds containing a $C_{8-18}$ alkyl chain, such as, for example, lauryltrimethylammonium chloride, cetyltrimethylammonium bromide, cetylpyridinium chloride, diisobutylphenoxyethoxyethyldimethylbenzylammonium chloride, coconut fatty acid alkyltrimethylammonium nitrite and cetylpyridinium fluoride.

Also suitable are benzylammonium chloride, benzyldimethylstearylammonium chloride and tertiary amines containing a $C_{1-18}$ hydrocarbon group and two (poly)oxyethylene groups.

Amphoteric surface-active agents are typically aliphatic secondary and tertiary amines, where the aliphatic radicals may be straight-chain or branched and in which one of the aliphatic radicals is a $C_{8-18}$ group and the other radical contains an anionic hydrophilic group, for example sulfonate, carboxylate, sulfates, phosphonate or phosphate.

The surface-active agent is usually incorporated into the oral-care formulation in an amount of 0-20% by weight, preferably 0-10% by weight.

Structure formers may be necessary in tooth creams or chewing gums in order to make possible the desired structural properties and desired "mouth feel". Suitable substances are, for example, natural gums, such as tragacanth gum, xanthan gum, karaya gum and gum arabic, algae derivatives, such as pearl moss and alginates, smectite earths, such as bentonite or hectorite, carboxyvinyl polymers and water-soluble cellulose derivatives, such as hydroxyethylcellulose and sodium carboxymethylcellulose. Improved structures can also be achieved if, for example, colloidal magnesium aluminium silicate is used. The structure former is typically present in the oral hygiene formulation in an amount of 0-5% by weight, preferably 0-3% by weight.

Abrasives should preferably be capable of cleaning and/or polishing the teeth without damaging the enamel or the dentine. They are usually used in tooth creams or tooth powders, but can also be used in mouthwashes, etc. Suitable abrasives are, for example, silica abrasives, such as hydrated silicates or silica gels, in particular silica xerogels (for example 'Syloid' available from W. R. Grace and Company). Likewise suitable are the silica materials available under the name 'Zeodent' from J. M. Huber Corporation, and diatomaceous earths, such as 'Celite' available from Johns-Manville Corporation. Alternative abrasives are alumina, insoluble metaphosphates, such as insoluble sodium metaphosphate, calcium carbonate, dicalcium phosphate (in dihydrate and anhydrous forms), calcium pyrophosphate, polymethoxylates and specific particulate curable polymerised resins, such as melamine-ureas, melamine-formaldehydes, urea-formaldehydes, melamine-urea-formaldehydes, crosslinked epoxides, melamines, phenolic resins, high-purity celluloses (for example 'Elcema' available from Degussa AG), and crosslinked polyesters. Abrasives are typically incorporated in the oral hygiene formulation in an amount of 0-80% by weight, preferably 0-60% by weight.

Suitable fluoride sources are, for example, sodium fluoride, zinc fluoride, potassium fluoride, aluminium fluoride, lithium fluoride, sodium monofluorophosphate, tin fluoride, ammonium fluoride, ammonium bifluoride and amine fluoride. The fluoride sources are preferably present in suitable amounts in order to provide about 50 ppm to about 4,000 ppm of fluoride ion on use.

Suitable desensitisers are, for example, formaldehyde, potassium nitrate, tripotassium citrate, potassium chloride and strontium chloride, strontium acetate and sodium citrate.

Flavours can be selected, for example, from oils of peppermint, spearmint, cranberry, sassafras root and clove. Sweeteners can also be used, for example D-tryptophan, saccharin, dextrose, aspartame, levulose, acesulframe, dihydrochalcones and sodium cyclamate. All these flavours are typically present in amounts of 0-5% by weight, preferably 0-2% by weight. Dyes and pigments can be added in order to make the formulation appear optically more attractive. Titanium dioxide is frequently used in order to obtain a strong white colour.

As described above, the dental and oral care formulations according to the invention may also comprise one or more further antimicrobial active compounds. Suitable examples thereof are zinc salts (such as zinc citrate), cetylpyridinium chloride, bisbiguanides (such as chlorhexidine), aliphatic amines, bromochlorophenes, hexachlorophenes, salicylanilides, quaternary ammonium compounds and triclosan. Alternatively, enzymatic systems can be employed, for example a system comprising lactoperoxidase and glucose oxidase can be used in order to generate antimicrobially effective amounts of hydrogen peroxide in the presence of glucose, water and oxygen.

The formulation may also comprise alcohol. This is particularly advantageous in mouthwashes.

Besides the compounds of the formula I and/or II and the ingredients described above, the preparations according to the invention may also comprise further ingredients. Further possible ingredients, in particular for cosmetic preparations, are described below.

The preparations according to the invention may additionally comprise at least one UV filter.

Organic UV filters, so-called hydrophilic or lipophilic sun-protection filters, are effective in the UVA region and/or UVB region and/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO 93/04665. Further examples of organic filters are indicated in the patent application EP-A 0 487 404. The said UV filters are usually named below in accordance with INCI nomenclature.

Particularly suitable for a combination are:

para-Aminobenzoic acid and derivatives thereof: PABA, Ethyl PABA, Ethyl dihydroxypropyl PABA, Ethylhexyl dimethyl PABA, for example marketed by ISP under the name "Escalol 507", Glyceryl PABA, PEG-25 PABA, for example marketed by BASF under the name "Uvinul P25".

Salicylates: Homosalate marketed by Merck under the name "Eusolex HMS"; Ethylhexyl salicylate, for example marketed by Symrise under the name "Neo Heliopan OS"; Dipropylene glycol salicylate, for example marketed by Scher under the name "Dipsal"; TEA salicylate, for example marketed by Symrise under the name "Neo Heliopan TS".

β,β-Diphenylacrylate derivatives: Octocrylene, for example marketed by Merck under the name "Eusolex® OCR"; "Uvinul N539" from BASF; Etocrylene, for example marketed by BASF under the name "Uvinul N35".

Benzophenone derivatives: Benzophenone-1, for example marketed under the name "Uvinul 400"; Benzophenone-2, for example marketed under the name "Uvinul D50"; Benzophenone-3 or oxybenzone, for example marketed under the name "Uvinul M40"; Benzophenone-4, for example marketed under the name "Uvinul MS40"; Benzophenone-9, for example marketed by BASF under the name "Uvinul DS-49"; Benzophenone-5, Benzophenone-6, for example marketed by Norquay under the name "Helisorb 11"; Benzophenone-8, for example marketed by American Cyanamid under the name "Spectra-Sorb UV-24"; Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3 -Benzylidenecamphor, for example marketed by Chimex under the name "Mexoryl SD"; 4-Methylbenzylidenecamphor, for example marketed by Merck under the name "Eusolex 6300"; Benzylidenecamphorsulfonic acid, for example marketed by Chimex under the name "Mexoryl SL"; Camphor benzalkonium methosulfate, for example marketed by Chimex under the name "Mexoryl SO"; terephthalylidenedicamphorsulfonic acid, for example marketed by Chimex under the name "Mexoryl SX"; Polyacrylamidomethylbenzylidenecamphor marketed by Chimex under the name "Mexoryl SW".

Phenylbenzimidazole derivatives: Phenylbenzimidazolesulfonic acid, for example marketed by Merck under the name "Eusolex 232"; disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole"; Methylenebis(benzotriazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: Ethylhexyltriazone, for example marketed by BASF under the name "Uvinul T150"; Diethylhexylbutamidotriazone, for example marketed by Sigma 3V under the name "Uvasorb HEB". Further triazine derivatives are by way of example 2,4,6-tris(diisobutyl 4'-aminobenzalmalonate)-s-triazine, or 2,4,6-Tris(biphenyl)-1,3,5-triazine, Butyl 4-({4-{[4-(butoxycarbonyl)phenyl]amino}-6-[(3-{1,3,3,3-tetramethyl-1-[(trimethylsilyl)oxy] disiloxanyl}propyl)amino]-1,3,5-triazin-2-yl}amino) benzoate, marketed under the name Mexoryl SBS. Structure of Mexoryl SBS:

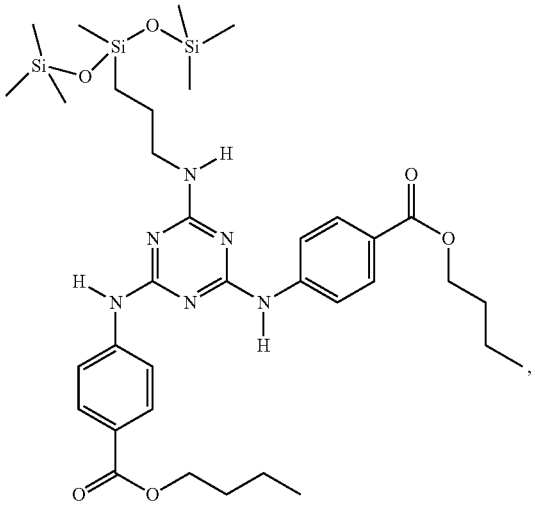

and Bis-ethylhexyloxyphenol methoxyphenyl triazine, for example marketed by BASF under the name Tinosorb S.

Anthraniline derivatives: Menthyl anthranilate, for example marketed by Symrise under the name "Neo Heliopan MA".

Imidazole derivatives: ethylhexyldimethoxybenzylidenedioxoimidazoline propionate.

Benzalmalonate derivatives: polyorganosiloxanes containing functional benzalmalonate groups, such as, for example, Polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl) benzoxazol-2-yl(4-phenyl)imino]-6-(2-ethylhexyl)imino-1,3,5-triazine, for example marketed by Sigma 3V under the name Uvasorb K2A, and mixtures comprising this.

piperazine derivatives, such as, for example, the compound

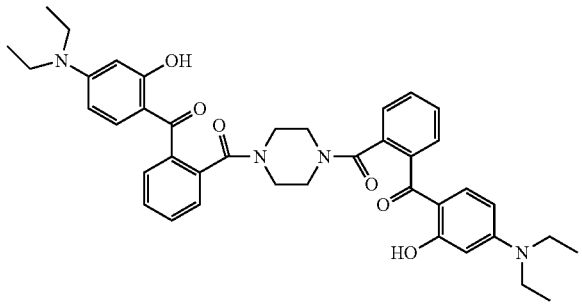

or the UV filters of the following structures

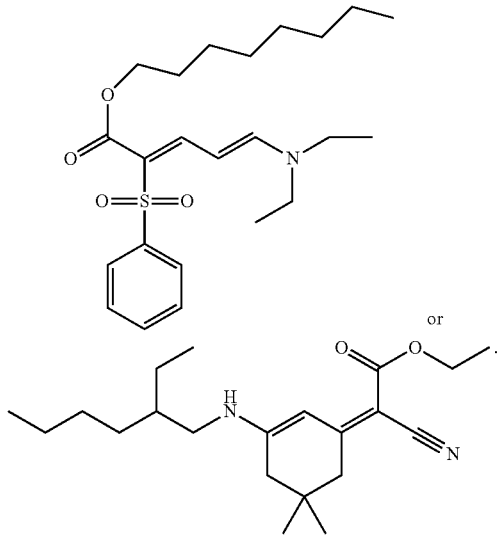

It is also possible to use UV filters based on polysiloxane copolymers having a random distribution in accordance with the following formula, where, for example, a=1.2; b=58 and c=2.8:

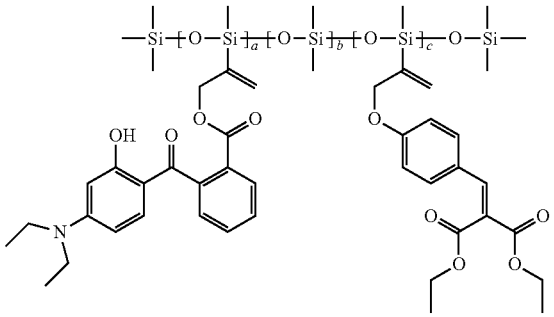

The compounds listed should only be regarded as examples, Other UV filters can of course also be used.

Suitable organic UV-protecting substances can preferably be selected from the following list: Ethylhexyl salicylate, Phenlbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-Bis[5-1 (dimethylpropyl)benzoxazol-2-yl(4-phenyl)imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Besides the extract and the optional organic UV filters, as described above, the preparations may comprise further inorganic UV filters, so-called particulate UV filters.

These combinations with particulate UV filters are possible both as powder and also as dispersion or paste of the following types.

Preference is given here both to those from the group of the titanium dioxides, such as, for example, coated titanium dioxide (for example Eusolex® T-2000, Eusolex® T-AQUA, Eusolex® T-AVO, Eusolex® T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments are greater than or equal to 200 nm, for example Hombitan® FG or Hombitan® FF-Pharma.

It may furthermore be preferred for the preparations to comprise inorganic UV filters which have been aftertreated by conventional methods, as described, for example, in Cosmetics & Toiletries, February 1990, Vol. 105, pp. 53 64. One or more of the following aftertreatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

Particulate UV filters which are preferably employed here are:

- untreated titanium dioxides, such as, for example, the products Microtitanium Dioxide MT 500 B from Tayca; titanium dioxide P25 from Degussa;
- Aftertreated micronised titanium dioxides with aluminium oxide and silicon dioxide aftertreatment, such as, for example, the product "Microtitanium Dioxide MT 100 SA from Tayca, or the product "Tioveil Fin" from Uniqema;
- Aftertreated micronised titanium dioxides with aluminium oxide and/or aluminium stearate/laurate aftertreatment, such as, for example, Microtitanium Dioxide MT 100 T from Tayca; Eusolex T-2000 from Merck;
- Aftertreated micronised titanium dioxides with iron oxide and/or iron stearate aftertreatment, such as, for example, the product "Microtitanium Dioxide MT 100 F" from Tayca;
- Aftertreated micronised titanium dioxides with silicon dioxide, aluminium oxide and silicone aftertreatment, such as, for example, the product "Microtitanium Dioxide MT 100 SAS", from Tayca;
- Aftertreated micronised titanium dioxides with sodium hexameta¬phosphate, such as, for example, the product "Microtitanium Dioxide MT 150 W" from Tayca.

The treated micronised titanium dioxides employed for the combination may also be aftertreated with:

- Octyltrimethoxysilanes, such as, for example, the product Tego Sun T 805 from Degussa;

Silicon dioxide; such as, for example, the product Parsol T-X from DSM;

Aluminium oxide and stearic acid; such as, for example, the product UV-Titan M160 from Sachtleben;

Aluminium and glycerine; such as, for example, the product UV-Titan from Sachtleben, Aluminium and silicone oils, such as, for example, the product UV-Titan M262 from Sachtleben;

Sodium hexamethaphosphate and polyvinylpyrrolidone,

Polydimethylsiloxanes, such as, for example, the product 70250 Cardre UF TiO2S13" from Cardre;

Polydimethylhydrogenosiloxanes, such as, for example, the product Microtitanium Dioxide USP Grade Hydrophobic" from Color Techniques.

The combination with the following products may furthermore also be advantageous:

Untreated zinc oxides, such as, for example, the product Z-Cote from BASF (Sunsmart), Nanox from Elementis;

Aftertreated zinc oxides, such as, for example, the following products:

"Zinc Oxide CS-5" from Toshibi (ZnO aftertreated with polymethylhydrogenosiloxane);

Nanogard Zinc Oxide FN from Nanophase Technologies;

"SPD-Z1" from Shin-Etsu (ZnO aftertreated with a silicone-grafted acrylic polymer, dispersed in cyclodimethylsiloxanes);

"Escalol Z100" from ISP (aluminium oxide-aftertreated ZnO, dispersed in an ethylhexyl methoxycinnamate/PVP-hexadecene/methicone copolymer mixture);

"Fuji ZNO-SMS-10" from Fuji Pigment (ZnO aftertreated with silicon dioxide and polymethylsilesquioxane);

Untreated cerium oxide micropigment, for example with the name "Colloidal Cerium Oxide" from Rhone Poulenc;

Untreated and/or aftertreated iron oxides with the name Nanogar from Arnaud.

By way of example, it is also possible to employ mixtures of various metal oxides, such as, for example, titanium dioxide and cerium oxide, with and without aftertreatment, such as, for example, the product Sunveil A from Ikeda. In addition, mixtures of aluminium oxide-, silicon dioxide- and silicone-aftertreated titanium dioxide/zinc oxide mixtures, such as, for example, the product UV-Titan M261 from Sachtleben, can also be used.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form.

The capsules in preparations to be employed in accordance with the invention are preferably present in amounts which ensure that the encapsulated UV filters are present in the preparation in the percent by weight ratios indicated above.

The preparations described, which, in accordance with the invention, comprise at least one compound of the formula I and/or II, may furthermore also comprise coloured pigments, where the layer structure of the pigments is not limited.

The coloured pigment should preferably be skin-coloured or brownish on use of 0.5 to 5% by weight. The choice of a corresponding pigment is familiar to the person skilled in the art.

Preferred preparations may likewise comprise at least one further cosmetic active compound, for example selected from antioxidants, anti-ageing, antiwrinkle, further antidandruff, further anti-acne, anticellulite active compounds, further deodorants, skin-lightening active compounds, self-tanning substances or vitamins.

With respect to the anti-acne action, synergistic combinations with further anti-acne active compounds, as disclosed, for example, in WO2009/098139 on page 47, line 2 to page 48, line 27 and DE10324567, are conceivable. Illustrative further anti-acne active compounds are silver particles and silver salts, such as silver lactate and silver citrate, azelaic acid, ellagic acid, lactic acid, glycolic acid, salicylic acid, glycyrrhizinic acid, triclosan, phenoxyethanol, hexamidine isethionate, ketoconazole, peroxides, such as hydrogen peroxide or benzoyl peroxide, 3-hydroxybenzoic acid, 4-hydroxybenzoic acid, phytic acid, arachidonic acid, caprylyl glycol, ethylhexylglycerol, farnesol, cetylpyridinium salts, 6-trimethylpentyl-2-pyridone (Piroctone Olamine) and lipohydroxy acid (LHA).

With respect to the antidandruff action, synergistic combinations with further antidandruff active compounds are conceivable, such as, for example, zinc pyrithione, Piroctone Olamine, selenium disulfide, Climbazole, Triclosan, Butylparaben, 1,3-Bis(hydroxymethyl)-5,5-dimethylimidazolidine-2,4-dione (DMDM Hydantoin), fumaric acid, Methylchloroisothiazolinone or Methylisothiazolinone (MIT), In their use in deodorants and antiperspirants, substances according to the invention can be combined synergistically with further deodorant adjuvants. To this end, reference is made to the active compounds mentioned in WO2011/131474. The following combinable active compounds are mentioned by way of example at this point: 2-Methyl 5-Cyclohexylpentanol, Aluminium Chlorohydrate, Ethylhexlglycerin, Farnesol, Aluminum Zirconium Tetrachlorohydrex GLY, Aluminium Chlorohydrate, Aluminium zirconium tetrachlorohydrate, Aluminum Sesquichlorohydrate (aluminum hydroxide chloride), Triclosan, Aluminum tetrachloride, Zinc Ricinoleate, Aluminum Zirconium Pentachlorohydrate, Polyaminopropyl Biguanide Stearate, Benzyl Salicylate, Aluminum Sesquichlorohydrat, Zinc PCA (zinc salt of pyrrolidonecarboxylic acid), zinc gluconate triethyl citrate, Aluminum Chloride, Aluminum Chlorohydrex Polyethylene Glycol Complex, Aluminum Chlorohydrex Propylene Glycol Complex, Aluminum Dichlorohydrate, Aluminum Dichlorohydrex Polyethylene Glycol Complex, Aluminum Dichlorohydrex Propylene Glycol Complex, Aluminum Sesquichlorohydrate, Aluminum Sesquichlorohydrex Polyethlene Glycol Complex, Aluminum Sesquichlorohydrex Propylene Glycol Complex, Aluminum Sulfate Buffered, Aluminum Zirconium Octachlorohydrate, Aluminum Zirconium Octachlorohydrex Glycine Complex, Aluminum Zirconium Pentachlorohydrate, Aluminum Zirconium Pentachlorohydrex Glycine Complex, Aluminum Zirconium Tetrachlorohydrate, Aluminum Zirconium Tetrachlorohydrex Glycine Complex, Aluminum Zirconium Trichlorhydrate, Aluminum Zirconium Trichlorohydrex Glycine Complex, Aluminum Zirconium Trichlorohydrex Glycine Complex, Aluminum Sulfate Buffered With Sodium Aluminum Lactate.

The protective action of preparations against oxidative stress or against the action of free radicals can be improved if the preparations comprise one or more antioxidants, where the person skilled in the art is presented with absolutely no difficulties in selecting suitably fast-acting or delayed-acting antioxidants.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysta sulfoximine, buthionine sulfones, penta-, hexa- and heptathionine sulfoximine) in very low tolerated doses (for example pmol to μmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA pentasodium ethylenediamine tetramethylene phosphonate and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), phytantriol, coenzyme Q10, vitamin A and derivatives (for example vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the formulae A or B

A

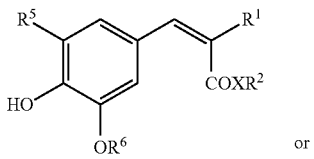

or

B

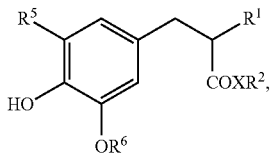

in which $R^1$ can be selected from the group —C(O)$CH_3$, —$CO_2R^3$, —C(O)$NH_2$ and —C(O)N$(R^4)_2$, X denotes O or NH, $R^2$ denotes linear or branched alkyl having 1 to 30 C atoms, $R^3$ denotes linear or branched alkyl having 1 to 20 C atoms, $R^4$ in each case, independently of one another, denotes H or linear or branched alkyl having 1 to 8 C atoms, $R^5$ denotes H, linear or branched alkyl having 1 to 8 C atoms or linear or branched alkoxy having 1 to 8 C atoms, and $R^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxybenzy)malonate (for example RonaCare® AP).

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with compounds according to the invention in percent by weight ratios in the range from 1000:1 to 1:1000, preferably in percent by weight ratios of 100:1 to 1:100.

Of the phenols which can be employed in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3'4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers and I. M. C. M. Rietjens (Free Radical Biology&Medicine 2001, 31(7), 869-881 investigate the pH dependence of the antioxidant action of hydroxyflavones. Quercetin exhibits the highest activity amongst the structures investigated over the entire pH range.

Besides the compounds of the formula I and/or II, the preparations may also comprise one or more further anti-ageing active compounds. Suitable anti-ageing active compounds, particular for skin-care preparations, are preferably so-called compatible solutes. These are substances which are involved in the osmoregulation of plants or microorganisms and can be isolated from these organisms. The generic term compatible solutes here also encompasses the osmolytes described in German patent application DE-A-

10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N-acetylornithine, trimethylamine N-oxide, di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof.

Additionally, anti-ageing active compounds which can be used are products from Merck, such as, for example, 5,7-dihydroxy-2-methylchromone, marketed under the trade name RonaCare®Luremine, Ronacare®Isoquercetin, Ronacare®Tilirosid or Ronacare®Cyclopeptide 5.

The preparations may also comprise one or more skin-lightening active compounds or synonymously depigmentation active compounds or melanogenesis inhibitors. Skin-lightening active compounds can in principle be all active compounds known to the person skilled in the art. Examples of compounds having skin-lightening activity are hydroquinone, kojic acid, arbutin, aloesin, niacinamide, azelaic acid, elagic acid, mulberry extract, magnesium ascorbyl phosphate, liquorice extract, emblica, ascorbic acid or rucinol.

Furthermore, the preparations according to the invention may comprise at least one self-tanning substance as further ingredient.

Advantageous self-tanning substances which can be employed are, inter alia:

1,3-dihydroxyacetone, glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or combination thereof.

The at least one further self-tanning substance is preferably present in the preparation in an amount of 0.01 to 20% by weight, particularly preferably in an amount of 0.5 to 15% by weight and very particularly preferably in an amount of 1 to 8% by weight, based on the total amount of the preparation.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight.

The present invention also relates to a process for the preparation of a preparation, as described above, characterised in that at least one compound of the formula I and/or II is mixed with a suitable vehicle and optionally with assistants and or fillers. Suitable vehicles and assistants or fillers are described in detail in the following part.

The said constituents of the preparation can be incorporated in the usual manner, with the aid of techniques which are well known to the person skilled in the art.

The cosmetic and dermatological preparations can be in various forms. Thus, they can be, for example, a solution, a water-free preparation, an emulsion or microemulsion of the water-in-oil (W/O) type or of the oil-in-water (O/W) type, a multiple emulsion, for example of the water-in-oil-in-water (W/O/W) or O/W/O type, a gel, a solid stick, an ointment or also an aerosol. Preference is given to emulsions. O/W emulsions are particularly preferred. Emulsions, W/O emulsions and O/W emulsions can be obtained in the usual manner.

The following, for example, may be mentioned as application form of the preparations to be employed: solutions, suspensions, emulsions, PIT emulsions, pastes, ointments, gels, creams, lotions, powders, soaps, surfactant-containing cleansing preparations, oils, aerosols plasters, compresses, bandages and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

A preferred solubiliser in general is 2-isopropyl-5-methylcyclohexanecarbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:

- mineral oils, mineral waxes
- oils, such as triglycerides of capric or caprylic acid, furthermore natural oils, such as, for example, castor oil;
- fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
- silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group branched and unbranched hydrocarbons and hydrocarbon waxes, silicone oils, dialkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

In a preferred embodiment, the preparations to be employed comprise hydrophilic surfactants. The hydrophilic surfactants are preferably selected from the group of the alkylglucosides, acyl lactylates, betaines and coconut amphoacetates.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth1-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cprinate, polyethylene glycol (20) glyceryl oleate, polyethylene glycol (20) glyceryl isostearate, polyethylene glycol (18) glyceryl oleate (cocoate).

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention: fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C¬ atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty bodies, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is generally made of the customary propellants, such as alkanes, fluoroalkanes and chlorofluoroalkanes, preferably alkanes.

The compounds of the formula I and/or II can in accordance with the invention also be used in foods. The further explanations given for foods also apply analogously to food supplements and to "functional food".

The foods which can be enriched in accordance with the present invention with one or more compounds of the formula I and/or II encompass all materials which are suitable for consumption by animals or for consumption by humans, for example vitamins and provitamins thereof, fats, minerals or amino acids". The foods may be solid, but also in liquid form, i.e. in the form of a drink.

Foods which can be enriched in accordance with the present invention with one or more compounds of the formula I and/or II are, for example, foods which originate from a single natural source (for example sugar, unsweetened juice, corn, cereals, cereal syrup), mixtures of foods of this type (for example multivitamin preparations, mineral mixtures or sweetened juice) or food preparations (for example prepared cereals, biscuits, mixed drinks, foods prepared yoghurt, diet foods, low-calorie foods or animal feeds). The foods which can be enriched in accordance with the present invention with one or more compounds of the formula I and/or II thus encompass all edible combinations of carbohydrates, lipids, proteins, inorganic elements, trace elements, vitamins, water or active metabolites of plants and animals.

The foods according to the invention which are enriched with one or more compounds of the formula I and/or II can be prepared with the aid of techniques which are well known to the person skilled in the art.

The present invention furthermore also relates to compounds of the formula Ia, Ib, IIa or IIb Ia

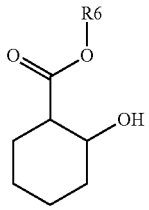

Ib

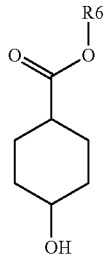

IIa

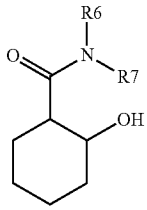

IIb

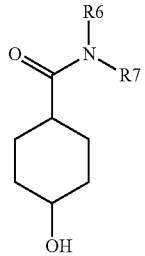

in which R6 and R7 stand, independently of one another, for a radical selected from

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, where the alkyl, alkenyl or alkynyl group may also contain one or more saturated or unsaturated $C_3$- to $C_{12}$-cycloalkyl groups, where compounds of the formula Ia in which R6 stands for H (compound I-11), methyl (compound I-1), ethyl (compound I-2), isopropyl (compound I-4), tert-butyl (compound I-5), n-hexyl (compound I-8), $CH_2CH(CH_2CH_3)_2$, $CH_2CH_2CH(CH_3)_2$, $C(=CH_2)CH_3$ or cyclopentyl are excluded, where compounds of the formula Ib in which R6 stands for H (compound I-25), methyl (compound I-15), ethyl (compound I-16), propyl (compound I-17), isopropyl (compound I-18) or tert-butyl (compound I-19) are excluded, where compounds of the formula IIa in which R6 stands for H and R7 stands for H, methyl, phenyl, p-tolyl, phenylmethyl or 2-phenylethyl or in which R6 and R7 simultaneously stand for ethyl are excluded, and where compounds of the formula IIb in which R6 and R7 simultaneously stand for H are excluded.

The radicals R6 and R7 are preferably defined as described above.

The compounds are particularly preferably selected from the following compounds:

I-3

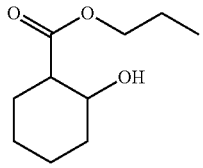

I-6

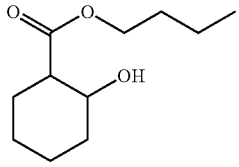

I-7

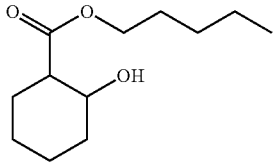

I-9

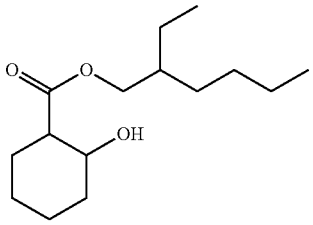

I-10

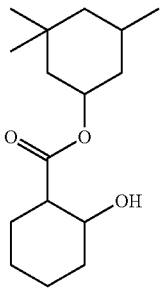

I-12

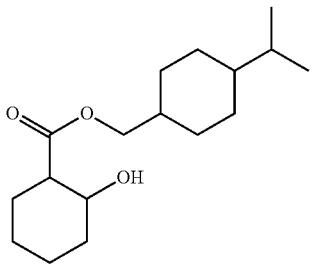

-continued
I-13
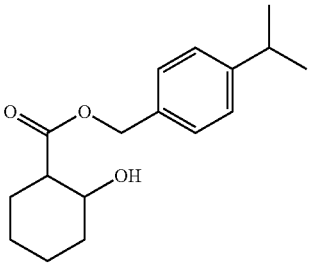
I-14
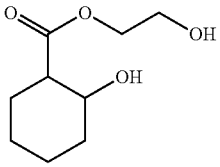
I-20
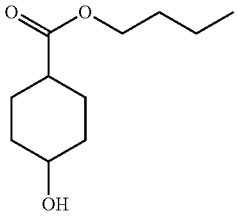
I-21
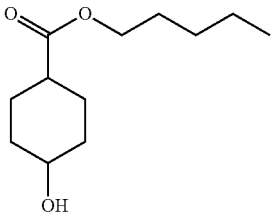
I-22
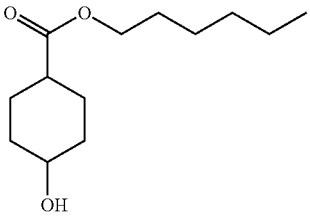
I-23
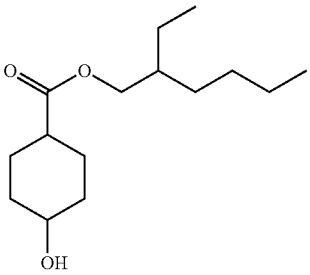
-continued
I-24
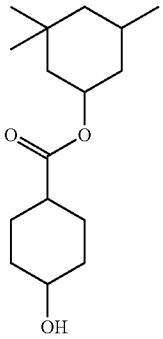
I-26
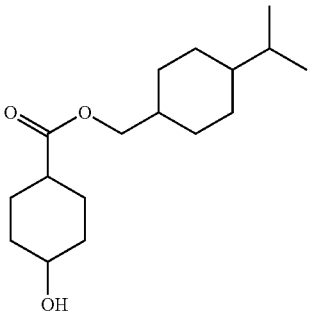
I-27
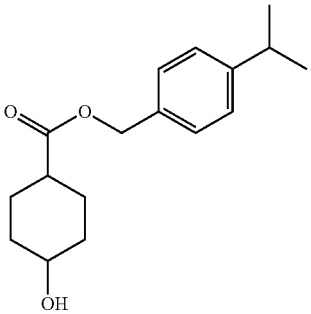
I-28
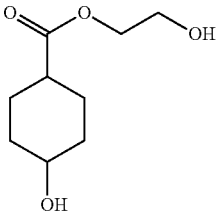
The present invention likewise relates to a process for the preparation of a compound of the formula Ia, Ib, Ic or Id, as described above, characterised in that a compound of the formula Ia-x, Ib-x, IIa-x or IIb-x
Ia-x
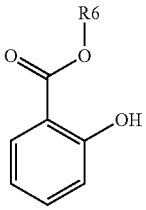

-continued

Ib-x

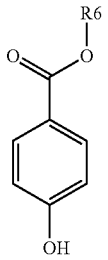

IIa-x

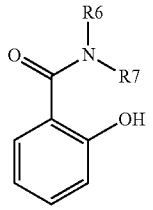

IIb-x

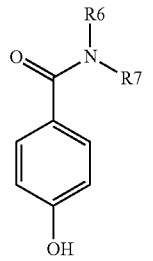

is converted into the corresponding hydrogenated product of the formula Ia, Ib, IIa or IIb by means of hydrogenation.

The hydrogenation here can be carried out as described above by methods known to the person skilled in the art using hydrogen and using a suitable catalyst.

The invention is explained in greater detail below with reference to examples. The invention can be carried out throughout the range claimed and is not restricted to the examples given here.

EXAMPLES

Example 1

Antioxidative Action

The antioxidative capacity of substances I-9, I-10 and I-2 is determined in the so-called Rancimate assay. The comparative substances used are 4-t-butyl-1-cyclohexanol and tocopherol. The positive standard employed is BHT. The measurement parameter is the time duration (induction time) of the increase in the conductivity of unstabilised soya oil on exposure to air at elevated temperature. The longer the induction time, the greater the stabilising or antioxidant action. The following boundary conditions were maintained: input of air 201/h; temperature 120° C. and sample concentrations of 0.1% w/w each in soya oil. For each test substance, a relative antioxidation-protection factor is determined, which corresponds to the ratio of the induction times with and without test substance:

Antioxidation-protection factor tocopherol: 1.00

Antioxidation-protection factor 4-t-butyl-1-cyclohexanol: 1.05

Antioxidation-protection factor substance I-9: 1.12

Antioxidation-protection factor substance I-10: 1.14

Antioxidation-protection factor substance I-2: 1.15

Antioxidation-protection factor positive standard BHT: 1.30

Example 2

Deodorant Action

Substances I-2 (of apple) and I-20 (of raspberry) have a pleasant inherent odour and are suitable for odour masking in deodorants.

Example 3

Antimicrobial Action Against Staphylococcus epidermis (Odour Control, Deodorant Efficacy)

For sample preparation, the substances being investigated are each dissolved or homogeneously dispersed in an amount of 1.0% in a water/ethanol mixture (12% of ethanol) and subsequently diluted with bacteria suspension in the ratio 1 to 2. S. epidermidis (ATCC 12228) is pre-incubated under aerobic conditions for 24 h at 35° C. on CASO agar (Merck 1.05458). A bacteria suspension having an optical density (OD) of about 1.0 is subsequently prepared in CASO broth (Merck 1.05459, double-concentrated) and diluted again 1:10 in CASO broth. 150 μl of freshly prepared sample are added to 150 μl of bacteria suspension per well. The optical density is determined over the course of time at 37° C. using a Bioscreen C™ analyser compared with the negative control (=vehicle without test substance). Compared with the negative control, reduced optical densities confirm growth-inhibiting substance actions Result as optical density of the bacteria suspension after an exposure time of 20 hours:

1st Experiment:

$OD_{20h}$(negative control): 0.80

$OD_{20h}$(substance I-2): 0.30

$OD_{20h}$(substance I-10): 0.30

2nd Experiment:

$OD_{20h}$(negative control): 0.65

$OD_{20h}$(substance I-9): 0.30

$OD_{20h}$(substance I-20): 0.20

Example 4

Antimicrobial Action Against Propionibacterium acnes (Acne Control)

For sample preparation, the substances being investigated are each dissolved or homogeneously dispersed in an amount of 1.0% in a water/ethanol mixture (12% of ethanol) and subsequently diluted with bacteria suspension in the ratio 1 to 2. P. acnes (ATCC 6919) is pre-incubated under anaerobic conditions for 48 h at 35° C. on RMC agar (Merck 1.05410). A bacteria suspension having an optical density (OD) of about 1.5 is subsequently prepared in RMC broth (Merck 1.05411, double-concentrated). 150 μl of freshly prepared sample and 100 μl of paraffin are added to 150 μl of bacteria suspension per well. The optical density is determined over the course of time at 37° C. using a Bioscreen C™ analyser compared with the negative control (=vehicle without test substance). Compared with the negative control, reduced optical densities confirm growth-inhibiting substance actions.

Result as optical density of the bacteria suspension after an exposure time of 20 hours:

$OD_{20h}$(negative control): 1.0

$OD_{20h}$(substance I-2): 0.45

$OD_{20h}$(substance I-9): 0.50

$OD_{20h}$(substance I-10): 0.45

$OD_{20h}$(substance I-20): 0.70

Example 5

Microbe Count Determination for Demonstration of the Bacteriostatic or Bactericidal Action For sample preparation, the substances being investigated are each dissolved or homogeneously dispersed in an amount of 1.0% in a water/ethanol mixture (12% of ethanol) (=sample). A bacteria suspension of S. epidermidis (ATCC 12228) having an optical density of 1.0 in CASO broth (Merck 1.05459) is diluted 1:10000 with CASO broth. 500 μl of sample are added to 500 μl of bacteria suspension, and the mixture is incubated at 35° C. for 24 h. After the incubation, the test batches are diluted to −6 in 10 unit steps, and 0.1 ml of each is plated-out on CASO agar (Merck 1.05458) and incubated at 35° C. for 24 h.

In order to determine the initial microbe count, 0.1 ml of the bacteria suspension used are plated-out on CASO agar (Merck 1.05458) and incubated at 35° C. for 24 h.

The colonies are subsequently counted, and the microbe count per ml is determined compared with the negative control (12% of ethanol in water).

Result:

| Test substance | Initial microbe count CFU/ml | Final microbe count CFU/ml | Note |
|---|---|---|---|
| I-10 | $3.8 \times 10^4$ | $2.0 \times 10^3$ | bacteriostatic |
| 1-9 | $3.8 \times 10^4$ | $2.0 \times 10^3$ | bacteriostatic |
| 1-2 | $3.8 \times 10^4$ | $2.9 \times 10^4$ | bacteriostatic |
| 1-20 | $3.8 \times 10^4$ | 0 | bactericidal |
| Negative control (12% aqueous ethanol solution) | $3.8 \times 10^4$ | $5.0 \times 10^7$ | — |

Example 6

Antimicrobial Action

The procedure corresponds to that described in Examples 4 and 5 using the microorganisms shown below. The concentrations indicated are the final use concentrations. In order to prepare the stock solution, double the final concentration were prepared in the solvent indicated. This was subsequently diluted 1:2 with the corresponding microbe suspension. In the case of Aspergillus brasiliensis, the microbe count determination was exceptionally carried out after 48 h.

| Substance | Conc. | Solvent | Microbe | Microbe count $t_0$ | Microbe count $t_{24\,h}$ | Δlog |
|---|---|---|---|---|---|---|
| 1-2 | 0.5% | $H_2O$ (12% of ethanol) | *Propionibacterium acnes* | $2.0 \times 10^4$ | $1.2 \times 10^4$ | −0.22 |
| 1-9 | 0.5% | $H_2O$ (12% of ethanol) | *Propionibacterium acnes* | $2.0 \times 10^4$ | $8.0 \times 10^2$ | −1.40 |
| — | — | $H_2O$ (12% of ethanol) | *Propionibacterium acnes* | $2.0 \times 10^4$ | $4.3 \times 10^6$ | +2.33 |
| 1-20 | 1.0% | $H_2O$ | *Propionibacterium acnes* | $7.8 \times 10^5$ | $1.3 \times 10^4$ | −1.78 |
| 1-2 + Phenoxy ethanol | 1.0% + 0.5% | $H_2O$ | *Propionibacterium acnes* | $7.8 \times 10^5$ | 0 | −5.89 |
| — | — | $H_2O$ | *Propionibacterium acnes* | $7.8 \times 10^5$ | $3.9 \times 10^8$ | +2.70 |
| 1-2 | 0.5% | $H_2O$ (12% of ethanol) | *Staphylococcus epidermidis* | $3.4 \times 10^4$ | $2.0 \times 10^4$ | −0.23 |
| 1-9 | 0.5% | $H_2O$ (12% of ethanol) | *Staphylococcus epidermidis* | $3.4 \times 10^4$ | $6.0 \times 10^3$ | −0.75 |
| — | — | $H_2O$ (12% of ethanol) | *Staphylococcus epidermidis* | $3.4 \times 10^4$ | $6.6 \times 10^7$ | +3.29 |
| 1-2 + Phenoxy ethanol | 1.0% + 0.5% | $H_2O$ | *Staphylococcus epidermidis* | $9.4 \times 10^4$ | $1.2 \times 10^4$ | −0.89 |
| — | — | $H_2O$ | *Staphylococcus epidermidis* | $9.4 \times 10^4$ | $1.9 \times 10^8$ | +3.31 |
| 1-2 | 0.5% | $H_2O$ (12% of ethanol) | *Corynebacterium xerosis* | $3.5 \times 10^4$ | 0 | −4.54 |
| 1-9 | 0.5% | $H_2O$ (12% of ethanol) | *Corynebacterium xerosis* | $3.5 \times 10^4$ | 0 | −4.54 |
| — | — | $H_2O$ (12% of ethanol) | *Corynebacterium xerosis* | $3.5 \times 10^4$ | $1.7 \times 10^6$ | +1.69 |
| 1-2 + Phenoxy ethanol | 1.0% + 0.5% | $H_2O$ | *Corynebacterium xerosis* | $6.9 \times 10^4$ | 0 | −4.84 |
| 1-2 + 1-9 | 0.5% + 0.5% | $H_2O$ | *Corynebacterium xerosis* | $6.9 \times 10^4$ | 0 | −4.84 |
| — | — | $H_2O$ | *Corynebacterium xerosis* | $6.9 \times 10^4$ | $8.7 \times 10^6$ | +2.10 |
| 1-9 | 0.125% | $H_2O$ | *Corynebacterium xerosis* | $1.0 \times 10^6$ | $5.0 \times 10^6$ | +0.70 |
| 1-20 | 0.5% | $H_2O$ | *Corynebacterium xerosis* | $1.0 \times 10^6$ | 0 | −6.00 |

-continued

| Substance | Conc. | Solvent | Microbe | Microbe count $t_0$ | Microbe count $t_{24\,h}$ | Δlog |
|---|---|---|---|---|---|---|
| — | — | $H_2O$ | *Corynebacterium xerosis* | $1.0 \times 10^6$ | $6.0 \times 10^8$ | +2.78 |
| 1-2 | 0.5% | $H_2O$ (12% of ethanol) | *Pseudomonas aeruginosa* | $6.8 \times 10^4$ | 0 | −4.83 |
| 1-9 | 0.5% | $H_2O$ (12% of ethanol) | *Pseudomonas aeruginosa* | $6.8 \times 10^4$ | $9.0 \times 10^3$ | −0.88 |
| — | — | $H_2O$ (12% of ethanol) | *Pseudomonas aeruginosa* | $6.8 \times 10^4$ | $1.0 \times 10^6$ | +1.17 |
| 1-2 + Phenoxy ethanol | 1.0% + 0.5% | $H_2O$ | *Pseudomonas aeruginosa* | $3.8 \times 10^5$ | 0 | −5.58 |
| — | — | $H_2O$ | *Pseudomonas aeruginosa* | $3.8 \times 10^5$ | $2.9 \times 10^9$ | +3.88 |
| 1-2 | 0.5% | $H_2O$ (12% of ethanol) | *Salmonella enterica* | $6.0 \times 10^4$ | 0 | −4.78 |
| 1-9 | 0.5% | $H_2O$ (12% of ethanol) | *Salmonella enterica* | $6.0 \times 10^4$ | $1.8 \times 10^4$ | −0.52 |
| — | — | $H_2O$ (12% of ethanol) | *Salmonella enterica* | $6.0 \times 10^4$ | $1.3 \times 10^8$ | +3.34 |
| Phenoxy ethanol | 0.4% | $H_2O$ (12% of ethanol) | *Salmonella enterica* | $1.3 \times 10^4$ | $8.2 \times 10^2$ | −1.20 |
| 1-2 + Phenoxy ethanol | 0.8% + 0.4% | $H_2O$ (12% of ethanol) | *Salmonella enterica* | $1.3 \times 10^4$ | 0 | −4.11 |
| 1-2 + 1-9 | 0.4% + 0.4% | $H_2O$ (12% of ethanol) | *Salmonella enterica* | $1.3 \times 10^4$ | 0 | −4.11 |
| 1-20 | 0.8% | $H_2O$ (12% of ethanol) | *Salmonella enterica* | $1.3 \times 10^4$ | 0 | −4.11 |
| — | — | $H_2O$ (12% of ethanol) | *Salmonella enterica* | $1.3 \times 10^4$ | $4.9 \times 10^7$ | +3.58 |
| 1-2 | 0.5% | $H_2O$ | *Salmonella enterica* | $1.0 \times 10^6$ | $5.0 \times 10^4$ | −1.30 |
| — | — | $H_2O$ | *Salmonella enterica* | $1.0 \times 10^6$ | $1.1 \times 10^9$ | +3.04 |
| 1-2 | 0.5% | $H_2O$ (12% of ethanol) | *Serratia marcescens* | $6.8 \times 10^4$ | 0 | −3.83 |
| 1-9 | 0.5% | $H_2O$ (12% of ethanol) | *Serratia marcescens* | $6.8 \times 10^4$ | $9.0 \times 10^3$ | −0.88 |
| — | — | $H_2O$ (12% of ethanol) | *Serratia marcescens* | $6.8 \times 10^4$ | $2.0 \times 10^7$ | +2.47 |
| Phenoxy ethanol | 0.5% | $H_2O$ | *Serratia marcescens* | $2.5 \times 10^5$ | $1.7 \times 10^3$ | −2.17 |
| 1-2 + Phenoxy ethanol | 1.0% + 0.5% | $H_2O$ | *Serratia marcescens* | $2.5 \times 10^5$ | 0 | −5.40 |
| — | — | $H_2O$ | *Serratia marcescens* | $2.5 \times 10^5$ | $8.8 \times 10^8$ | +3.55 |
| 1-2 | 0.5% | $H_2O$ | *Serratia marcescens* | $2.9 \times 10^5$ | $9.0 \times 10^5$ | +0.49 |
| — | — | $H_2O$ | *Serratia marcescens* | $2.9 \times 10^5$ | $9.7 \times 10^8$ | +3.52 |
| 1-2 | 0.5% | $H_2O$ (12% of ethanol) | *Candida albicans* | $3.4 \times 10^4$ | $3.0 \times 10^2$ | −2.05 |
| 1-9 | 0.5% | $H_2O$ (12% of ethanol) | *Candida albicans* | $3.4 \times 10^4$ | $1.5 \times 10^1$ | −3.36 |
| — | — | $H_2O$ (12% of ethanol) | *Candida albicans* | $3.4 \times 10^4$ | $1.8 \times 10^6$ | +1.72 |
| 1-20 | 1.0% | $H_2O$ (12% of ethanol) | *Candida albicans* | $6.0 \times 10^3$ | 0 | −3.78 |
| — | — | $H_2O$ (12% of ethanol) | *Candida albicans* | $6.0 \times 10^3$ | $5.0 \times 10^5$ | +1.92 |
| 1-2 | 0.5% | $H_2O$ | *Candida albicans* | $3.8 \times 10^5$ | $2.5 \times 10^5$ | −0.18 |
| 1-9 | 0.5% | $H_2O$ | *Candida albicans* | $3.8 \times 10^5$ | $8.0 \times 10^6$ | +1.32 |
| 1-20 | 0.5% | $H_2O$ | *Candida albicans* | $3.8 \times 10^5$ | 0 | −5.58 |
| — | — | $H_2O$ | *Candida albicans* | $3.8 \times 10^5$ | $3.0 \times 10^7$ | +1.90 |
| 1-2 | 0.5% | $H_2O$ (12% of ethanol) | *Echerichia coli* | $4.6 \times 10^4$ | $1.8 \times 10^3$ | −1.41 |
| 1-9 | 0.5% | $H_2O$ (12% of ethanol) | *Echerichia coli* | $4.6 \times 10^4$ | $3.8 \times 10^2$ | −2.08 |
| — | — | $H_2O$ (12% of ethanol) | *Echerichia coli* | $4.6 \times 10^4$ | $1.5 \times 10^7$ | +2.51 |
| Methyl-paraben | 0.2% | $H_2O$ (12% of ethanol) | *Echerichia coli* | $6.3 \times 10^4$ | $4.8 \times 10^3$ | −1.12 |
| 1-2 + Methyl-paraben | 0.4% + 0.2% | $H_2O$ (12% of ethanol) | *Echerichia coli* | $6.3 \times 10^4$ | 0 | −4.80 |

-continued

| Substance | Conc. | Solvent | Microbe | Microbe count $t_0$ | Microbe count $t_{24\,h}$ | Δlog |
|---|---|---|---|---|---|---|
| Phenoxy ethanol | 0.4% | $H_2O$ (12% of ethanol) | *Echerichia coli* | $6.3 \times 10^4$ | $2.0 \times 10^1$ | −3.50 |
| 1-2 + Phenoxy ethanol | 0.8% + 0.4% | $H_2O$ (12% of ethanol) | *Echerichia coli* | $6.3 \times 10^4$ | 0 | −4.80 |
| 1-20 | 0.8% | $H_2O$ (12% of ethanol) | *Echerichia coli* | $6.3 \times 10^4$ | 0 | −4.80 |
| — | — | $H_2O$ (12% of ethanol) | *Echerichia coli* | $6.3 \times 10^4$ | $5.8 \times 10^7$ | +2.96 |
| 1-9 | 0.5% | $H_2O$ (12% of ethanol) | *Staphylococcus aureus* | $4.2 \times 10^4$ | $1.4 \times 10^2$ | −2.48 |
| — | — | $H_2O$ (12% of ethanol) | *Staphylococcus aureus* | $4.2 \times 10^4$ | $2.0 \times 10^8$ | +3.68 |
| Phenoxy ethanol | 0.5% | $H_2O$ (12% of ethanol) | *Staphylococcus aureus* | $7.2 \times 10^4$ | $7.0 \times 10^1$ | −3.01 |
| 1-2 + Phenoxy ethanol | 1.0% + 0.5% | $H_2O$ (12% of ethanol) | *Staphylococcus aureus* | $7.2 \times 10^4$ | 0 | −4.86 |
| 1-2 + 1-9 | 0.5% + 0.5% | $H_2O$ (12% of ethanol) | *Staphylococcus aureus* | $7.2 \times 10^4$ | $6.0 \times 10^1$ | −3.80 |
| — | — | $H_2O$ (12% of ethanol) | *Staphylococcus aureus* | $7.2 \times 10^4$ | $9.0 \times 10^7$ | +3.10 |
| 1-20 | 0.5% | $H_2O$ (12% of ethanol) | *Staphylococcus aureus* | $1.1 \times 10^4$ | 0 | −4.04 |
| — | — | $H_2O$ (12% of ethanol) | *Staphylococcus aureus* | $1.1 \times 10^4$ | $3.0 \times 10^7$ | +3.44 |
| 1-2 | 0.5% | $H_2O$ (12% of ethanol) | *Aspergillus brasiliensis* | $2.0 \times 10^4$ | $1.0 \times 10^4$ | −0.30 |
| 1-9 | 0.5% | $H_2O$ (12% of ethanol) | *Aspergillus brasiliensis* | $2.0 \times 10^4$ | $8.0 \times 10^2$ | −1.40 |
| — | — | $H_2O$ (12% of ethanol) | *Aspergillus brasiliensis* | $2.0 \times 10^4$ | $3.0 \times 10^5$ | +1.18 |
| Phenoxy ethanol | 0.5% | $H_2O$ (12% of ethanol) | *Aspergillus brasiliensis* | $8.0 \times 10^2$ | $4.0 \times 10^2$ | −0.30 |
| 1-2 + Phenoxy ethanol | 1.0% + 0.5% | $H_2O$ (12% of ethanol) | *Aspergillus brasiliensis* | $8.0 \times 10^2$ | $3.0 \times 10^1$ | −1.43 |
| 1-20 | 1.0% | $H_2O$ (12% of ethanol) | *Aspergillus brasiliensis* | $8.0 \times 10^2$ | $2.0 \times 10^2$ | −0.60 |
| — | — | $H_2O$ (12% of ethanol) | *Aspergillus brasiliensis* | $8.0 \times 10^2$ | $1.2 \times 10^4$ | +1.18 |
| 1-2 | 1.0% | $H_2O$ | *Malassezia furfur* | $4.0 \times 10^2$ | 0 | −2.60 |
| 1-20 | 1.0% | $H_2O$ | *Malassezia furfur* | $4.0 \times 10^2$ | 0 | −2.60 |
| — | — | $H_2O$ | *Malassezia furfur* | $4.0 \times 10^2$ | $3.0 \times 10^4$ | +1.86 |

Example 7

Synthesis of 2-hydroxycyclohexanecarboxylic acid 2-ethylhexyl ester (Substance I-9)

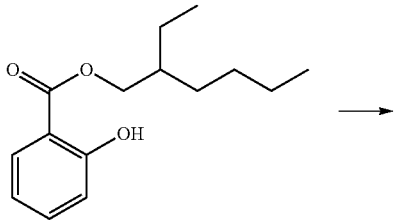

-continued

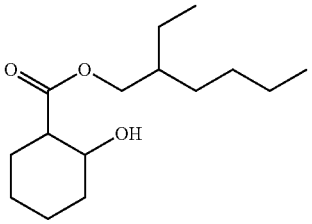

50 g of 2-hydroxybenzoic acid 2-ethylhexyl ester (Euso-lex® OS) are dissolved in 318 ml of 2-propanol. 5 g of 5% Rh/C catalyst (53.6% of water) are subsequently added. The hydrogenation is carried out using hydrogen 3.0 at 65° C. and 5 bar pressure. When the hydrogenation is complete, the catalyst is separated off by filtration. The filtrate is freed from the solvent in vacuo and filtered through a syringe filter (0.2 μm). The analytically pure product is obtained as colourless oil in a mixture of cis and trans isomers in the ratio of about 5/1.

Example 8

Synthesis of 2-hydroxycyclohexanecarboxylic acid 3,3,5-trimethylcyclohexyl ester (Substance I-10)

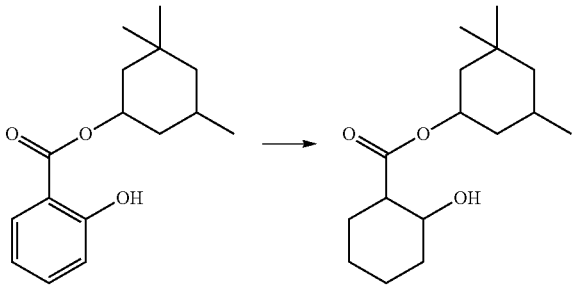

50 g of 3,3,5-trimethylcyclohexyl ester (Eusolex® HMS) are dissolved in 318 ml of 2-propanol. 5 g of 5% Rh/C catalyst (53.6% of water) are subsequently added. The hydrogenation is carried out using hydrogen 3.0 at 80° C. and 5 bar pressure. When the hydrogenation is complete, the catalyst is separated off by filtration. The filtrate is filtered through Seitz filters (a) 0.5 μm, subsequently b) 0.2 μm). The filtrate is freed from the solvent in vacuo. Analytically pure product is obtained as colourless oil in a mixture of cis and trans isomers in the ratio of about 5/1.

Example 9

Synthesis of 4-hydroxycyclohexanecarboxylic acid butyl ester (Substance I-20)

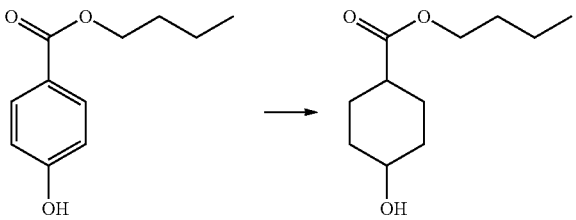

30 g of 4-hydroxybenzoic acid butylyl ester are dissolved in 100 ml of tetrahydrofuran. 3.0 g of 5% Rh/C catalyst (about 50% of water) are subsequently added. The hydrogenation is carried out using hydrogen 3.0 at 65° C. and 5 bar. When the hydrogenation is complete, the catalyst is separated off by filtration. The filtrate is freed from the solvent in vacuo. Analytically pure product is obtained as colourless oil in a mixture of cis and trans isomers of about 5/2.

Example 10

Measurement of the Dynamic Viscosities in Order to Estimate the Spreadability at 25° C.

After measurement of the densities and kinematic viscosities using an Ubbelohde viscometer, the following dynamic viscosities arise:

Kinematic viscosity of I-2: 15.5 $mm^2/s$

Density of I-2: 1.0564 $g/cm^3$; 25° C.

Dynamic viscosity of I-2=kinematic viscosity of I-2× density I-2=16.4 [mPas]

Kinematic viscosity of I-9: 33.0 $mm^2/s$

Density of I-9: 0.9752 $g/cm^3$; 25° C.

Dynamic viscosity of I-9=kinematic viscosity of I-9× density of I-9=32.2 [mPas]

Since spreadabilities and viscosities of cosmetic emollients correlate well, good spreadabilities can be concluded from the viscosities determined.

Example A

Antidandruff Shampoo

| INCI | % (w/w) | % (w/w) | % (w/w) | % (w/w) | % (w/w) | % (w/w) |
|---|---|---|---|---|---|---|
| Acrylates/C10-30 Alkyl Acrylate Crosspolymer | 1.0 | 1.0 | 1.0 | 1.0 | 1.0 | 1.0 |
| Propyleneglycol | 5.0 | 5.0 | 5.0 | 5.0 | 5.0 | 5.0 |
| Sodium Lauryl Sulfate (30%) | 15.0 | 15.0 | 15.0 | 15.0 | 15.0 | 15.0 |
| Sodium Laureth Sulfate (28%) | 15.0 | 15.0 | 15.0 | 15.0 | 15.0 | 15.0 |
| Cocamidopropyl betaine (35%) | 5.0 | 5.0 | 5.0 | 5.0 | 5.0 | 5.0 |
| Substance 1-2 | 0.5 | 0.5 | | 1.0 | | |
| Substance 1-9 | | 0.5 | | | 0.75 | 2.0 |
| Substance 1-10 | | | 0.5 | 1.0 | | |
| Substance 1-20 | | | 0.5 | | 0.75 | |
| Polyquaternium-10 | 0.30 | 0.30 | 0.30 | 0.30 | 0.30 | 0.30 |
| DMDM hydantoin (and) Iodopropynyl Butylcarbamate | 0.3 | 0.3 | 0.3 | 0.3 | 0.3 | 0.3 |
| Polyquaternium-39 | 1.0 | 1.0 | 1.0 | 1.0 | 1.0 | 1.0 |
| Dimethicone PEG-7 Isostearate | 0.5 | 0.5 | 0.5 | 0.5 | 0.5 | 0.5 |
| Zinc Pyrithione (48%) | 2.0 | 1.0 | 1.0 | | 0.5 | 0.5 |
| Fragrance | 1.0 | 1.0 | 1.0 | 1.0 | 1.0 | 1.0 |
| Dye | 0.1 | 0.1 | 0.1 | 0.1 | 0.1 | 0.1 |
| Aqua | to 100 | to 100 | to 100 | to 100 | to 100 | to 100 |
| Sodium Hydroxide | q.s. to pH 6 | q.s. to pH 6 | q.s. to pH 6 | q.s. to pH 6 | q.s. to pH 6 | q.s. to pH 6 |

Example B

Anti-Acne Face-Cleansing Gel

| INCI | % (w/w) | % (w/w) | % (w/w) | % (w/w) | % (w/w) | % (w/w) |
|---|---|---|---|---|---|---|
| Propylene Glycol | 2.5 | 2.5 | 2.5 | 2.5 | 2.5 | 2.5 |
| Dehydroxanthan Gum | 1.5 | 1.5 | 1.5 | 1.5 | 1.5 | 1.5 |
| Cocamidopropyl Betaine | 10.0 | 10.0 | 10.0 | 10.0 | 10.0 | 10.0 |
| Salicylic acid | 2.0 | 0.5 | 0.5 | 1.0 | | |
| Sodium Lactate | 0.5 | 1.0 | | | | 1.0 |
| Triclosan | 0.2 | | | | 0.2 | |
| 1,3.Butylene glycol | 3.5 | 3.5 | 3.5 | 3.5 | 3.5 | 3.5 |
| Substance 1-2 | 0.5 | 0.5 | | 1.0 | 1.0 | |
| Substance 1-9 | | 0.5 | | | 0.75 | 2.0 |
| Substance 1-10 | | | 0.5 | 1.0 | | |
| Substance 1-20 | | | 0.5 | | | |
| Menthyl Lactate | 0.2 | 0.2 | 0.2 | 0.2 | 0.2 | 0.2 |
| PEG-40 Hydrogenated Castor Oil | 0.5 | 0.5 | 0.5 | 0.5 | 0.5 | 0.5 |
| C8-16-decyl Glucoside | 5.0 | 5.0 | 5.0 | 5.0 | 5.0 | 5.0 |
| DMDM Hydantoin (and) Iodopropynyl Butylcarbamate | 0.5 | 0.5 | 0.5 | 0.5 | 0.5 | 0.5 |

-continued

| INCI | % (w/w) | % (w/w) | % (w/w) | % (w/w) | % (w/w) | % (w/w) |
|---|---|---|---|---|---|---|
| Lactose (and) Cellulose (and) Hydroxypropyl Methylcellulose (and) Ultramarine Blue (C177007) (and) Triclosan | 0.4 | 0.4 | 0.4 | 0.4 | 0.4 | 0.4 |
| Fragrance | 0.5 | 0.5 | 0.5 | 0.5 | 0.5 | 0.5 |
| Aqua | to 100 | to 100 | to 100 | to 100 | to 100 | to 100 |

Example C

Antiperspirant Spray (Aerosol)

a) Suspension preparation

| INCI | % (w/w) | % (w/w) | % (w/w) | % (w/w) | % (w/w) | % (w/w) |
|---|---|---|---|---|---|---|
| Aluminium Chlorohydrate | 35.0 | 25.0 | 20.0 | 10.0 | 25.0 | |
| Ethylhexyl glycerin | 0.5 | 0.5 | 0.5 | 0.5 | 0.5 | 0.5 |
| C12-15 Alkylbenzoate | 5.0 | 5.0 | 5.0 | 5.0 | 5.0 | 5.0 |
| Diasteardimonium Hectorite | 5.0 | 5.0 | 5.0 | 5.0 | 5.0 | 5.0 |
| Silver citrate | 0.0015 | 0.0025 | | | | |
| Silver lactate | | | 0.0025 | 0.0015 | | |
| Propylene carbonate | 1.0 | 1.0 | 1.0 | 1.0 | 1.0 | 1.0 |
| Substance 2 | | | | 1.0 | 1.5 | |
| Substance 9 | 0.5 | 1.0 | 2.0 | 1.0 | | 3.5 |
| Substance 10 | 2.0 | 1.5 | 0.5 | 1.0 | | 1.0 |
| Substance 21 | | | | 1.0 | 1.5 | |
| Fragrance | 4.0 | 4.0 | 4.0 | 4.0 | 4.0 | 4.0 |
| Cyclopentasiloxane | to 100 | to 100 | to 100 | to 100 | to 100 | to 100 |

b) Propellant-gas mixture comprising propane/isobutane/butane (1/1/1)

c) The aerosol is prepared by packaging the suspension in an aerosol can together with the propellant gas in the suspension/propellant gas ratio=20/80.

Example D

Antiperspirant/Deodorant (Gel)

| Ingredients | % (w/w) | % (w/w) | % (w/w) | % (w/w) | % (w/w) | % (w/w) |
|---|---|---|---|---|---|---|
| Aluminium Zirconium Octachloro hydrex GLY | 10.0 | 15.0 | 20.0 | 10.0 | 15.0 | |
| Alcohol denat. | 5.0 | 5.0 | 5.0 | 5.0 | 5.0 | 5.0 |
| Cyclomethicone | 15.0 | 15.0 | 10.0 | 20.0 | 10.0 | 20.0 |
| Propylene Glycol | 10.0 | 5.0 | 5.0 | 15.0 | 5.0 | 15.0 |
| Dimethicone | 2.5 | 2.5 | 2.5 | 2.5 | 2.5 | |
| Trisiloxane | 5.0 | 2.5 | 2.5 | 5.0 | 2.5 | 5.0 |
| Substance 2 | | | | 1.0 | 1.5 | |
| Substance 9 | 0.5 | 1.0 | 2.0 | 1.0 | | 3.5 |
| Substance 10 | 2.0 | 1.5 | 0.5 | 1.0 | | 1.0 |
| Substance 21 | | | | 1.0 | 1.5 | |
| Maltosin | 0.1 | 0.1 | 0.1 | 0.1 | 0.1 | 0.5 |
| Calcium Chloride | 0.3 | 0.3 | 0.3 | 0.3 | 0.3 | 0.3 |
| PEG/PPG-18/18 Dimethicone | 0.75 | 0.75 | 0.75 | 0.75 | 0.75 | 0.75 |
| Fragrance | qs | qs | qs | qs | qs | qs |
| Water | To 100 | To 100 | To 100 | To 100 | To 100 | To 100 |

Example E

Antiperspirant/Deodorant (Roll-On)

| Ingredients | % (w/w) | % (w/w) | % (w/w) | % (w/w) | % (w/w) | % (w/w) |
|---|---|---|---|---|---|---|
| Aluminium Chlorohydrate | 25.0 | 25.0 | 25.0 | 25.0 | 25.0 | 25.0 |
| Isoceteth-20 | 1.5 | 1.5 | 1.5 | 1.5 | 1.5 | 1.5 |
| Mineral Oil | 3.0 | 3.0 | 3.0 | 3.0 | 3.0 | 3.0 |
| Butylene Glycol | 2.0 | 2.0 | 2.0 | 2.0 | 2.0 | 2.0 |
| Glyceryl Isostearate | 1.5 | 1.5 | 1.5 | 1.5 | 1.5 | 1.5 |
| Laureth-7 Citrate | 1.0 | 1.0 | 1.0 | 1.0 | 1.0 | 1.0 |
| Palmitamidopropyl Trimonium Chloride | 0.3 | 0.3 | 0.3 | 0.3 | 0.3 | 0.3 |
| Propylene Glycol | 0.5 | 0.5 | 0.5 | 0.5 | 0.5 | 0.5 |
| PEG-150 Distearate | 0.3 | 0.3 | 0.3 | 0.3 | 0.3 | 0.3 |
| Substance 2 | | | | 1.0 | 1.5 | |
| Substance 9 | 0.5 | 1.0 | 2.0 | 1.0 | 3.5 | |
| Substance 10 | 2.0 | 1.5 | 0.5 | 1.0 | 1.0 | |
| Substance 21 | 1.0 | 1.5 | | | | |
| Calcium Chloride | 0.3 | 0.3 | 0.3 | 0.3 | 0.3 | 0.3 |
| PEG/PPG-18/18 Dimethicone | 0.75 | 0.75 | 0.75 | 0.75 | 0.75 | 0.75 |
| Fragrance | qs | qs | qs | qs | qs | qs |
| Water | to 100 | to 100 | to 100 | to 100 | to 100 | to 100 |

Example F

Anti-Acne Composition

The following composition variants comprise substances according to the invention in use concentration of in each case between 0.1 and 10 percent by weight. Ingredients are indicated in accordance with INCI.

Variant a)

water, TEA-cocoate, cocamide DEA, potassium cocoate, TEA-laurate/myristate, butylene glycol, glycerin, glycol distearate, PEG-55 stearate, sodium cocoamphoacetate, chocolate vine (akebia quinata) root extract, scutellaria baicalensis root extract, chinese blackberry extract, angelica acutiloba root extract, coix lacryma-jobi (job's tears) seed extract, sodium polyaspartate, melothria heterophylla extract, disodium EDTA, trisodium EDTA, ethanol, xanthan gum, citric acid, sodium methyl cocoyl taurate, squalane, Hydroxypropyl Methylcellulose, polyquaternium-10, lauryl betaine, sodium bisulfite, sodium chloride, phenoxyethanol, methylparaben, fragrance Variant b)

Aqua, Cyclohexasiloxane, Isononyl Isononanoate, Propylene Glycol, Isohexadecane, Niacinamide, PEG_100 stearate, Glyceryl Stearate, Cetyl Alcohol, Kaolin, Salicylic Acid, proctone olamine, Acrylates Copolymer, PEG-4, PEG-4 Dilaurate, PEG-4 Laurate, Sodium Carbomer, Capryloyl Glycine, Capryloyl Salicylic Acid, Xanthan Gum, Isobutane, Sodium Sulfate, Iodopropynyl Butylcarbamate, Chlorhexidine Digluconate, Parfum (Perfuming)

Variant c)

Aqua, Nylon-66, Glycerin, Cyclohexasiloxane, aluminum starch octenylsucinate, PEG-2 Stearate, Prunus Armeniaca Fruit, dydrogenated polyisobutene, Cetearyl Alcohol, Triethanolamine, Salicylic Acid, Silica, Kaolin, PEG-100 Stearate, C13-14 Isoparaffin, Stearyl Alcohol, Hamamelis Virginian Extract, hamaelis virginiana, glyceril stearate, Sarcosine, ć glycine soja, Methylparaben, Arginine PCA, Phenoxyethanol, Cinnamomum Zeylanicum Leaf Extract, Tocopherol, Alcohol, Disodium EDTA, Capryloyl Glycine, Laureth-7, oleth-1, Acrylates/stearyl Acrylate/dimethicone Methacrylate Copolymer, Polyacrylamide, Butylene Glycol, CI 42090, Parfum (Perfuming)

Variant d)

Aqua, Glycerin, Cyclohexasiloxane, Hydrogenated Polyisobutene (Hydrogenated), Niacinamide, Isopropyl Lauroyl Sarcosinate, Ammonium Polyacryloyldimethyl Taurate, Silica, Methyl Methacrylate Crosspolymer, Sodium Hydroxide, Salicylic Acid, Nylon-12, Zinc PCA, Linoleic Acid, Pentaerythrityl Tetra-di-t-butyl Hydroxyhydrocinnamate, Capryloyl Glycine, Capryloyl Salicylic Acid, Caprylyl Glycol, Piroctone Olamine, Myristyl Myristate, Potassium Cetyl Phosphate, Glyceryl Stearate SE, Parfum (Perfuming), F.I.L B36611/1

Variant e)

Salicylic Acid, (Aqua), D1-C 12-13 alkyl malate, Cyclohexasiloxane, Propylene Glycol, Aluminum Starch Octenylsuccinate, PEG-100 Stearate, Glyceryl Stearate, Cetyl Alcohol, PEG-4 Dilaurate, PEG-4 Laurate, Zinc PCA, Sodium Hydroxide, Capryloyl Salicylic Acid, Xanthan Gum, acrylates C10-30 alky acrylate crosspolymer, Iodopropynyl Butylcarbamate, PEG-4, Parfum (Perfuming)

Variant f)

Resorcinol, Tocopherol, acetate, Stearyl Glycyrrhetinate, Pyridoxine HCl, Cinchona Succirubra Bark Extract (Extract), Glycerin (Concentrate), Butylene Glycol, Carbomer, Hydroxypropyl Methylcellulose, Propylene Glycol Alginate, polyoxyethylene hydrogenated castor oil, Alcohol, Triethanolamine, Aqua (Purified), Disodium EDTA, Methylparaben, Propylparaben, BHT, Parfum (Perfuming)

Variant g)

biosulfur fluid, Dipotassium Glycyrrhizate, Aqua, Butylene Glycol, hydrolysed rice leaf extract, Phellodendron Amurense Bark Extract (Extract), Hydroxyproline, Salvia Officinalis Leaf Extract (Extract), Camellia Sinensis Leaf (Extract), Rosmarinus Officinalis Extract (Extract), Glycerin (Cosmetic Grade), Pentylene Glycol, Carbomer, Xanthan Gum, Camphor, Menthol, Potassium Hydroxide Alcohol Denat., Aqua, Acrylates/C10-30 Alkyl Acrylate Crosspolymer, Hamamelis Virginiana Extract, Laminaria Saccharina Extract (Extract), Salicylic Acid, Sucrose, Caffeine, Butylene Glycol, Benzalkonium Chloride, ILN 32308

Variant h)

Aqua, Alcohol Denat., Glycerin, Acrylates/C10-30 Alkyl Acrylate Crosspolymer, Triethanolamine, Salicylic Acid, Dipotassium Glycyrrhizate, Copper Gluconate, Zinc Gluconate, Potassium Alum, Vitreoscilla Ferment (Extract), Pentylene Glycol, Sodium Citrate, Parfum (Perfuming), Limonene, Benzyl Benzoate, Linalool, Alpha-isomethyl Ionone, F.I.L. B28365/2

Variant i)

Alcohol, Aqua, Polyacrylamide, C13-14 Isoparaflin, Laureth-7, Hamamelis Virginiana Water, Glycerin, Salicylic Acid, Cyclopentasiloxane, C12-15 Alkyl Lactate, Phenoxyethanol, Cetyl Lactate, dipropylene glycol isoceteth-20 acetate, Cocamidopropyl PG-dimonium Chloride Phosphate, Polysorbate 20, Phenethyl Dimethicone, Dehydroxanthan Gum, Parfum (Perfuming), Benzalkonium Chloride, Propylene Glycol, Ammonium Hydroxide, T-butyl Alcohol, Tetrasodium EDTA, Capryloyl Glycine, Sarcosine, Cinnamomum Zeylanicum Bark Extract (Extract), Portulaca Oleracea Extract (Extract), Cedrus Atlantica Bark Extract (Extract), Denatonium Benzoate Variant j)

Alcohol, Aqua, Propylene Glycol, PEG-6, Salicylic Acid, PPG-33 Butyl Ether, Potassium Hydroxide, Benzophenone-1, Parfum (Perfuming), BHT, Isopropyl Myristate, Disodium EDTA, Lysine Carboxymethyl Cysteinate, Isododecane, Aloe Barbadensis Leaf Juice, Sodium C8-16 Isoalkylsuccinyl Lactoglobulin Sulfonate, Polystyrene/hydrogenated Polyisopentene Copolymer (Hydrogenated), Chamomilla Recutita Flower Extract (Extract), CI 42090, CI 17200

Variant k)

Aqua, Polyethylene, Hydrogenated Vegetable Oil (Hydrogenated, Vegetable Based), Hydrogenated Polydecene (Hydrogenated), Stearyl Alcohol, Glycerin, Glyceryl Stearate, Alcohol, PEG-40 Stearate, C12-15 Pareth-12, Cetyl Alcohol, Hamamelis Virginiana Extract (Extract), Menthol, Parfum (Perfuming), Benzethonium Chloride, Sorbic Acid, BHT, CI 15985, Eucalyptus Globulus Leaf Extract (Extract), CI 47005, CI 42090, Disodium EDTA Variant l)

Aqua, Alcohol, PPG-5-ceteth-20, Glycerin, Salicylic Acid, Parfum (Perfuming), Methyl Lactate, Denatonium Benzoate Variant m)

Aqua, Alcohol Denat., Dipropylene Glycol, Glycerin, Salicylic Acid, Laminaria Saccharina Extract Variant n)

Polyoxyethylene ethers, Lauramine Oxide, Polyethylene (Granules), Propylene Glycol, benzalconium chlorate, Alcohol, Potassium Sorbate, Silica, yellow CI 47005, Parfum (Perfuming), Aqua (Purified)

Variant o)

Aqua, sodium sulfonate C14-16 olefin, Cocamidopropyl Betaine, salicilic acid, Glycerin, Decyl Glucoside, alkyl C12-13 potassium phosphate, Acrylates Copolymer, glycol distearate/laureth-4/cocamidopropyl betaine, Parfum (Perfuming), Citric Acid, portulaca oleracea (little hogweed) extract, Cedrus Atlantica Bark Extract (Extract), caprylyl glycine/sarcosine/cinnamomum zeylanicum (ceylon cinnamon) bark extract, Sodium Hydroxide Variant p)

Aqua, Kaolin, Glycerin, Butylene Glycol, Zea Mays Starch, CI 77891, Decyl Glucoside, Polyethylene, Sodium Laureth Sulfate, Chondrus Crispus, PEG-7 Glyceryl Cocoate, Jojoba Esters, Phenoxyethanol, Salicylic Acid, Tetrasodium EDTA, Xanthan Gum, Triethanolamine, Methylparaben, Zinc Gluconate, Menthol, Butylphenyl Methylpropional, CI 77007, Propylene Glycol, Limonene, Linalool, Eucalyptus Globulus Leaf Extract (Extract), Parfum (Perfuming), F.I.L. B32440

Variant q)

Aqua, Sodium C14-16 Olefin Sulfonate, Glycerin, Cocamidopropyl Betaine, Salicylic Acid, Sodium Methyl Cocoyl Taurate, Acrylates Copolymer, Sodium Lauroamphoacetate, Parfum (Perfuming), Citric Acid, Glycol Distearate, Sodium Chloride, Menthyl Lactate, Cocamidopropyl PG-dimonium Chloride Phosphate Variant r)

Aqua, Aqua, Decyl Glucoside, Polysorbate 20, Ceteareth-60 Myristyl Glycol, Disodium Cocoamphodiacetate, Glycerin, Sodium Lauroyl Sarcosinate, Methyl Gluceth-20, Benzoic Acid, Cetrimonium Bromide, curcurbita pepo seed oil, Disodium EDTA, Parfum (Perfuming), CI 61570, Lactic Acid, Phenoxyethanol, CI 19140, Zinc Gluconate Variant s)

Aqua, Cyclomethicone, Propylene Glycol, Glycerin, Polyacrylamide, Polymethyl Methacrylate, Aqua, C13-14

Isoparaffin, Zinc Gluconate, Butylparaben, Cetrimonium Bromide, cucurbita pepo (pumpkin) seed oil (cucurbita pepo), Dimethiconol, Disodium EDTA, Parfum (Perfuming), Laureth-7, Pyridoxine HCl, Salicylic Acid, Triethanolamine Variant t)

Aqua, Cetyl Alcohol, Cyclomethicone, Polysorbate 60, Glycolic Acid, Aqua, SD Alcohol 39-C, Polymethyl Methacrylate, Sodium Hydroxide, Cetearyl Alcohol, Arginine HCl, BHT, Ceteareth-33, Dimethiconol, Parfum (Perfuming), Potassium Sorbate, CI 17200, retinal undecyl rhamnoside Variant u)

Aqua, Cyclohexasiloxane, Isononyl Isononanoate, Propylene Glycol, Isohexadecane, Niacinamide, PEG 100 stearate, Glyceryl Stearate, Cetyl Alcohol, Kaolin, Salicylic Acid, proctone olamine, Acrylates Copolymer, PEG-4, PEG-4 Dilaurate, PEG-4 Laurate, Sodium Carbomer, Capryloyl Glycine, Capryloyl Salicylic Acid, Xanthan Gum, Isobutane, Sodium Sulfate, Iodopropynyl Butylcarbamate, Chlorhexidine Digluconate, Parfum (Perfuming)

Variant v)

Aqua, Dipropylene Glycol, SD Alcohol 39-C, Zinc Gluconate, cucurbita pepo pump-kin seed oil (cucurbita pepo), Parfum (Perfuming), PEG-40 Hydrogenated Castor Oil (Hydrogenated), PPG-26-buteth-26, Salicylic Acid, Silica, Stearalkonium Hectorite, Triethanolamine, Aqua Variant w)

Aqua, Glycerin, Kaolin, Bentonite, Sodium Methyl Cocoyl Taurate, CI 77891, Trideceth-9, Salicylic Acid, C12-15 Alkyl Lactate, Sodium Chloride, Menthol, PEG-5 Ethylhexanoate, Xanthan Gum, Cetyl Lactate, Cocamidopropyl PG-dimonium Chloride Phosphate, Coconut Acid (Coconut Derived), Citric Acid, Sodium Citrate, Lactic Acid, Disodium EDTA, Methylparaben, Chlorphenesin, Propylparaben, Benzalkonium Chloride, Ethylparaben, Parfum (Perfuming)

Variant x)

Aqua, Cocamidopropyl Betaine, Sodium Myreth Sulfate, Acrylates Copolymer, Lactic Acid, Maris Limus Extract, ostera, Lauryl Glucoside, PEG-40 Hydrogenated Castor Oil (Hydrogenated), PEG-200 Hydrogenated Glyceryl Palmate (Hydrogenated), Polyethylene, Mannitol, Trisodium EDTA, Polyquaternium-10, Benzophenone-4, Microcrystalline Cellulose, Propylene Glycol, Phenoxyethanol, Methylparaben, Propylparaben, Alpha-isomethyl Ionone, Citronellol, Hexyl Cinnamal, Benzyl Salicylate, Butylphenyl Methylpropional, Parfum (Perfuming), CI 42090, CI 74160

Variant y)

Aqua, Sodium Laureth Sulfate, PEG-8, Coco-betaine, Hexylene Glycol, Sodium Chloride, PEG-120 Methyl Glucose Dioleate, Zinc PCA, Sodium Hydroxide, Citric Acid, Sodium Benzoate, Phenoxyethanol, Caprylyl Glycol, Parfum (Perfuming), F.I.L. B32026/1

Variant aa)

Aqua, Kaolin, Glycerin, Butylene Glycol, Zea Mays Starch, CI 77891, Decyl Glucoside, Polyethylene, Sodium Laureth Sulfate, Chondrus Crispus, PEG-7 Glyceryl Cocoate, Salicylic Acid, Eucalyptus Globulus Leaf Extract (Extract), Menthol, Zinc Gluconate, Jojoba Esters, Propylene Glycol, Triethanolamine, Xanthan Gum, Tetrasodium EDTA, Methylparaben, Phenoxyethanol, CI 7707

Variant ab)

Aqua, Alcohol Denat., Sorbitol, Cocamidopropyl Betaine, Parfum (Perfuming), Allantoin, Sodium Chloride, Propylene Glycol, Laminaria Digitata Extract (Extract)

Variant ac)

Aqua, Sodium Myreth Sulfate, Disodium Laureth Sulfosuccinate, Cocamidopropyl Betaine, PEG-150 Distearate, Coco-glucoside, Glyceryl Oleate, Hexylene Glycol, Sorbitol, Cymbopogon Schoenanthus Extract (Extract), 1,10-decanediol, 10-hydroxydecanoic Acid, Sebacic Acid, Parfum (Perfuming), PEG-7 Glyceryl Cocoate, Tocopherol, Hydrogenated Palm Glycerides Citrate (Hydrogenated), Propylene Glycol, Butylene Glycol, Citric Acid, Sodium Chloride, Sodium Salicylate, Sodium Benzoate Variant ad)

Aqua, PPG-15 Stearyl Ether, Glycerin, Stearyl Alcohol, Cetyl Betaine, Salicylic Acid, Distearyldimonium Chloride, Polyethylene, Sodium Lauryl Sulfate, Cetyl Alcohol, Alcohol, Steareth-21, Sodium Chloride, Sodium Hydroxide, Synthetic Wax (Artificial), Behenyl Alcohol, PPG-30, Steareth-2, Parfum (Perfuming), Dipropylene Glycol, Mica, Benzyl Salicylate, Limonene, Disodium EDTA, BHT, CI 77891, CI 77510

Variant ae)

Aqua, Alcohol Denat., Glucosamine, Sorbitol, Sea Whip Extract (Extract), CI 77120, 10-hydroxydecanoic Acid, silica disodium EDTA, benzalkonium chloride (ILN32341) nylon-12, Salicylic Acid, Butylene Glycol, Hamamelis Virginiana Extract, Laminaria Saccharina Extract (Extract), Caffeine, Sucrose, Glycerin, acetyl Variant af)

Aqua, Glycerin, Butylene Glycol, Sodium Methyl Cocoyl Taurate, Sucrose, Salicylic Acid, Disodium Phosphate, Arginine Cocoate, Laminaria Saccharina Extract (Extract), Cola Nitida Seed Extract (Extract, Seed), Caffeine, Algae Extract (Extract), Mentha Piperita Leaves, Sea Whip Extract (Extract), PEG/PPG-18/18 Dimethicone, Sodium Hyaluronate, PPG-6-decyltetradeceth-30, Lactobacillus Ferment, Stearamidopropyl Dimethylamine, Longifolene, Acetyl Glucosamine, Capryloyl Glycine, perilla aldehyde, 10-hydroxydecanoic Acid, Polyquaternium-7, beta-caryophylene, Phospholipids, Sodium Salicylate, Sodium Stearate, Disodium EDTA, Phenoxyethanol, chloroxylenol (ILN 32338)

Variant ag)

Benzoyl Peroxide 2.5%. Inactive: Water, cyclopentasiloxane, butylene glycol, ceteareth-20, dimenthicone, sucrose, green tea leaf extract, barley extract, acetyl glucosamine, lactobacillus ferment, poria cocos sclerotium extract, laminaria saccharina extract, polymethyl methacrylate, gentian root extract, sunflower seedcake, saccharomyces lysate extract, astrocaryum murumuru butter, acrylamide/sodium acryloyldimethyltaurate copolymermyristyl alcohol, glycerin Variant ae)

Benzoyl Peroxide, inactive (Glycerin), Petrolatum, Paraffinum Liquidum, C12-15 Alkyl Benzoate, Aqua, Sodium Cocoyl Isethionate, Sodium C14-16 Olefin Sulfonate, Zinc Lactate, Acrylates/C10-30 Alkyl Acrylate Crosspolymer, Menthol, Parfum (Perfuming), potassium polymetaphosphate, CI 77891, Carbomer Variant af)

Aqua, Sodium C14-16 Olefin Sulfonate, Cocamidopropyl Betaine, Linoleamidopropyl PG-dimonium Chloride Phosphate, Polysorbate 20, Anthemis Nobilis Flower Extract (Extract), Citrus Grandis Fruit Extract (Extract), Aloe Barbadensis Flower Extract (Extract), Chamomilla Recutita Flower Extract (Extract), C12-15 Alkyl Lactate, cocamidopropyl, PG-dimonium chloride phosphate, Polyquaternium-7, Ascorbyl Palmitate, Propylene Glycol, Sodium Benzotriazolyl Butylphenol Sulfonate, PEG-120 methyl glucose dioleate PEG-80 sorbitan laurate, Disodium EDTA, Sodium Chloride, Benzalkonium Chloride, CI 16035, CI 60725, fragrance (963-277)

Variant ag)

Salicylic Acid, (Aqua), Cyclopentasiloxane, PEG-8, Dimethicone, Dimethicone Crosspolymer, Sodium Polyacrylate, Vinyl Dimethicone/methicone Silsesquioxane Crosspolymer, cocamidopropyl PG dimonium chloride phosphate, Cucumis Sativus Fruit Extract (Extract), Camellia Sinensis Leaf Extract (Extract), Glycerin, Panthenol, Butylene Glycol, C12-15 Alkyl Lactate, Cetyl Alcohol, Glyceryl Stearate, Cetyl Lactate, PEG 75 stearate, Ceteth-20, Steareth-20, Trideceth-6, Cyclopentasiloxane, PEG/PPG-18/18 Dimethicone, Sclerotium Gum, Laureth-23, Laureth-4, Disodium EDTA, Benzalkonium Chloride, Potassium Hydroxide, CI 61570, CI 19140, CI 42090, Parfum (Perfuming)

Variant ah)

Benzoyl Peroxide, inactive, Aqua, Bentonite, Caprylic/Capric Triglyceride, Glycerin, Emulsifying Wax (National Formulary, Emulsifying), Polysorbate 20, Glyceryl Laurate, Cetyl Dimethicone, Magnesium Aluminum Silicate, Xanthan Gum, Sodium Citrate, Disodium EDTA, Citric Acid, Methylparaben, Propylparaben Variant ai)

Polyquaternium-37, Silica, Aqua, Glycerin, Polysilicone-13, PEG-12 Dimethicone, Hamamelis Virginiana Extract (Extract), CI 77891, Stearyl Glycyrrhetinate, Butylene Glycol, Methylparaben Variant aj)

Salicylic Acid, Aqua, Sodium Cocoyl Isethionate, Cetearyl Alcohol, Laureth-3, Glycerin, Coconut Acid (Coconut Derived), Sodium Isethionate, Sodium Hydroxide, Parfum (Perfuming), Lavandula Stoechas Extract (Extract), Helichrysum Italicum Extract (Extract), Cistus Monspeliensis Extract (Extract), Disodium EDTA, PEG-40 Hydrogenated Castor Oil (Hydrogenated), Phenoxyethanol, Methylparaben, Butylparaben, Ethylparaben, Isobutylparaben, Propylparaben Variant ak)

Aqua, Ethylhexyl Methoxycinnamate, Ethylhexyl Salicylate, Benzophenone-3, Butyl Methoxydibenzoylmethane, Propylene Glycol, C12-15 Alkyl Benzoate, Dimethicone, Glyceryl Stearate, Thiodipropionic Acid, Retinyl Palmitate, Triticum Vulgare Germ Extract (Extract, Germs), Saccharomyces/zinc Ferment, Glycolic Acid, Salicylic Acid, Pyridoxine HCl, Tocopherol, Palmitoyl Oligopeptide, Palmitoyl Tetrapeptide-7, Glycerin, Aluminum Starch Octenylsuccinate, Hydroxyethyl Acrylate/Sodium Acryloyldimethyl Taurate Copolymer, Silica, Isohexadecane, Acrylates Crosspolymer, PEG-100 Stearate, Caprylyl Glycol, Hydrogenated Polyisobutene (Hydrogenated), Hydroxyethylcellulose, Xanthan Gum, Choleth-24, Polysorbate 60, Ceteth-24, Isododecane, Sorbitan Isostearate, Polystyrene/hydrogenated Polyisopentene Copolymer (Hydrogenated), Butylene Glycol, Carbomer, Polysorbate 20, Steareth-2, Ammonium Hydroxide, Cetyl Alcohol, Stearic Acid, Disodium EDTA, Phenoxyethanol, Parfum (Perfuming).

The invention claimed is:

1. A method for achieving an antimicrobial effect in a host in need thereof, comprising administering to a host in need thereof an effective amount of at least one compound of the formula I and/or II

I

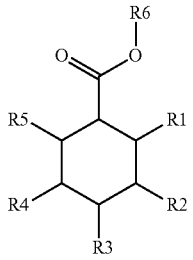

II

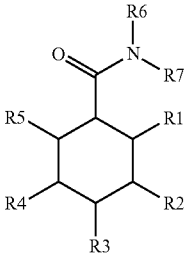

in which R1, R2, R3, R4 and R5 stand, independently of one another, for a radical selected from H, OH, $OCOCH_3$, $O—(CH_2—CH_2—O)_n—CH_2—CH_2—OH$, where n=0 to 20, straight-chain or branched alkyl or alkoxy group having 1 to 20 C atoms, where at least one of the radicals R1, R2, R3, R4 and R5 stands for OH, $OCOCH_3$ or $O—(CH_2—CH_2—O)_n—CH_2—CH_2—OH$, where n=0 to 20, and in which R6 and R7 stand, independently of one another, for a radical selected from

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, where the alkyl, alkenyl or alkynyl group may also contain one or more saturated or unsaturated $C_3$- to $C_{12}$-cycloalkyl groups, with the proviso the following compound is excluded:

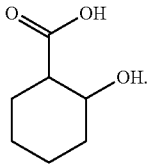

2. The method according to claim 1 comprising administering in the form of cosmetic or pharmaceutical formulations, medicinal products or foods.

3. The method according to claim 2 comprising administering in the form of a dental or oral care product.

4. The method according to claim 1, wherein the radicals R1, R2, R3, R4 and R5 stand, independently of one another, for H or OH, where 1, 2 or 3 of the radicals R1, R2, R3, R4 and R5 stand for OH.

5. The method according to claim 4, wherein the compound of the formula I and II is a compound of formula Ia, Ib, IIa and IIb Ia

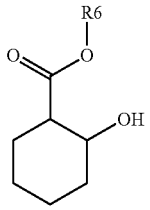

Ib

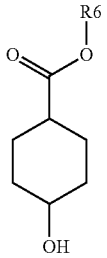

IIa

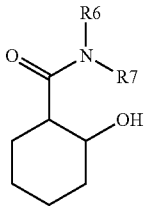

IIb

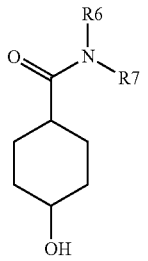

in which R6 and R7 stand, independently of one another, for

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, where the alkyl, alkenyl or alkynyl group may also contain one or more saturated or unsaturated $C_3$- to $C_{12}$-cycloalkyl groups.

6. The method according to claim 1, wherein the radicals R6 and R7 stand for

H, $CH_2—CH_2—OH$, straight-chain or branched alkyl group having 1 to 10 C atoms, which may also contain a saturated or unsaturated $C_6$-cycloalkyl group.

7. The method according to claim 6, wherein the compound of the formula I is a compound selected from formulae I-1 to I-10 and I-12 to I-28

I-1

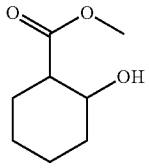

I-2

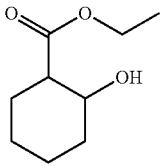

I-3

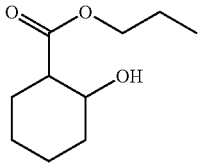

I-4

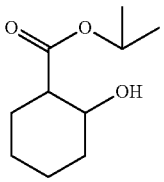

I-5

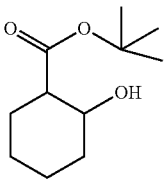

I-6

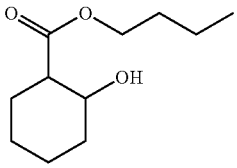

I-7

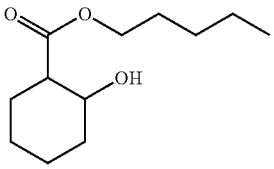

I-8

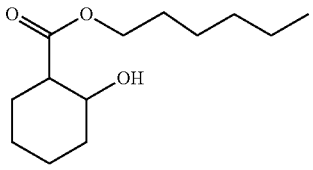

-continued
I-9
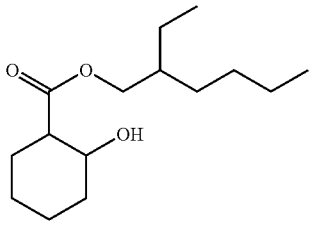
I-10
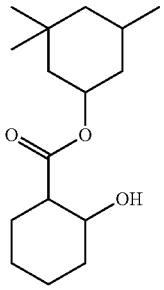
I-12
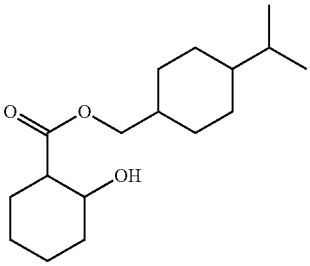
I-13
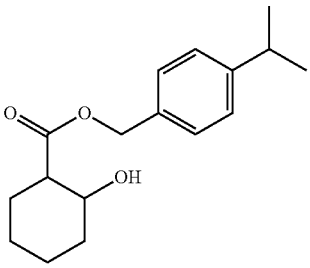
I-14
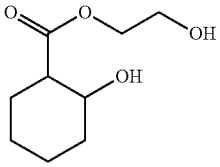
I-15
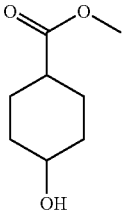
-continued
I-16
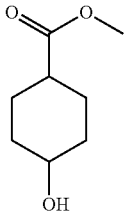
I-17
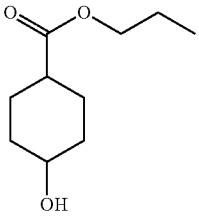
I-18
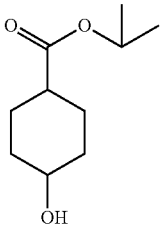
I-19
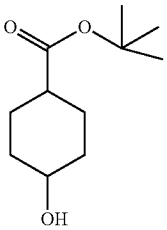
I-20
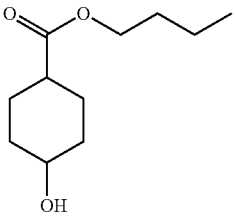
I-21
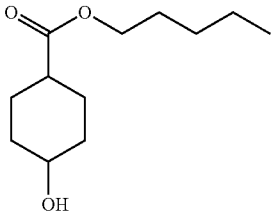
I-22
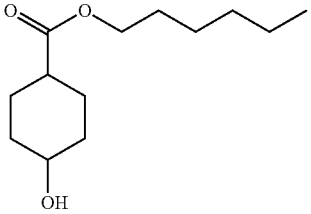

-continued

I-23

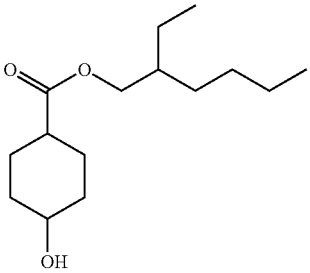

I-24

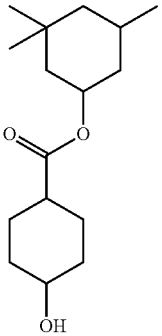

I-25

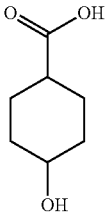

I-26

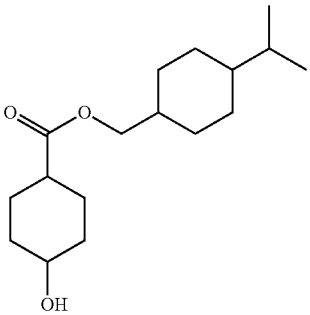

I-27

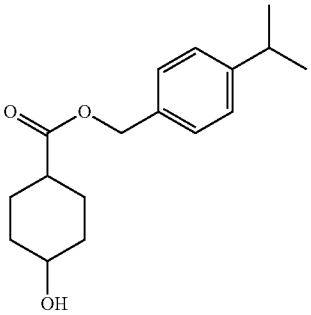

-continued

I-28

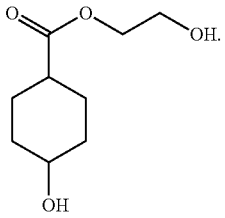

8. A method for achieving an antimicrobial effect in a subject, comprising administering to a subject in need thereof an anti-acne, antidandruff, antiperspirant or deodorant formulation containing an effective amount of at least one compound of the formula I and/or II

I

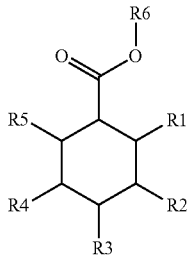

II

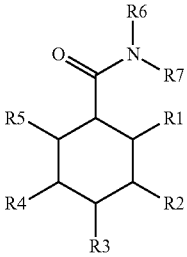

in which R1, R2, R3, R4 and R5 stand, independently of one another, for a radical selected from H, OH, $OCOCH_3$, $O—(CH_2—CH_2—O)_n—CH_2—CH_2—OH$, where n=0 to 20, straight-chain or branched alkyl or alkoxy group having 1 to 20 C atoms, where at least one of the radicals R1, R2, R3, R4 and R5 stands for OH, $OCOCH_3$ or $O—(CH_2—CH_2—O)_n—CH_2—CH_2—OH$, where n=0 to 20, and in which R6 and R7 stand, independently of one another, for a radical selected from

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, where the alkyl, alkenyl or alkynyl group may also contain one or more saturated or unsaturated $C_3$- to $C_{12}$-cycloalkyl groups.

*9. The method according to claim 1, wherein an effective amount of at least one compound of the formula I is administered to said host.*

10. The method according to claim 9, wherein the radicals R1, R2, R3, R4 and R5 stand, independently of one another, for H or OH, where 1, 2 or 3 of the radicals R1, R2, R3, R4 and R5 stand for OH.

11. The method according to claim 10, wherein said compound of formula I is a compound of formula Ia or Ib:

Ia

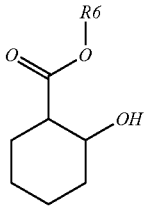

Ib

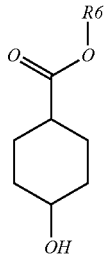

in which R6 stands for

H, $(CH_2—CH_2—O)_n—CH_2—CH_2—OH$, where n=0 to 20, straight-chain or branched alkyl group having 1 to 20 C atoms, straight-chain or branched alkenyl or alkynyl group having 2 to 20 C atoms and one or more double or triple bonds, wherein the alkyl, alkenyl and alkynyl groups each optionally contain one or more saturated or unsaturated $C_3$- to $C_{12}$-cycloalkyl groups.

12. The method according to claim 11, wherein the R6 stands for

H, $CH_2—CH_2—OH$, straight-chain or branched alkyl group having 1 to 10 C atoms, which optionally contains a saturated or unsaturated $C_6$-cycloalkyl group.

13. The method according to claim 12, wherein the compound of the formula I is a compound selected from formulae I-15 to I-28

I-15

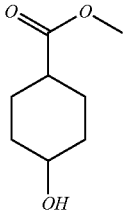

-continued

I-16

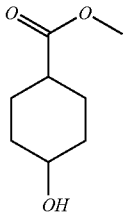

I-17

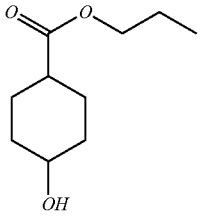

I-18

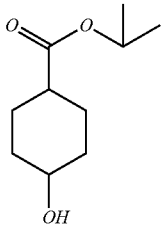

I-19

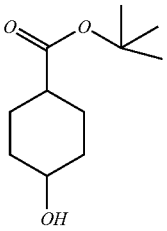

I-20

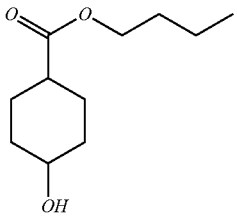

I-21

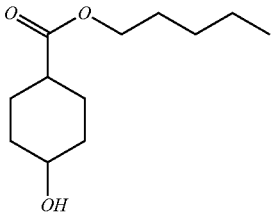

I-22

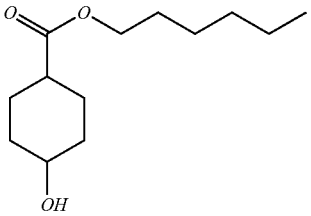

-continued

I-23

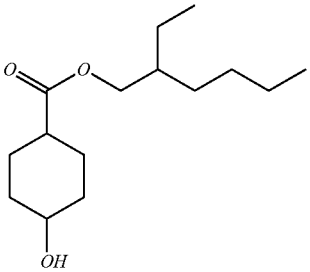

I-24

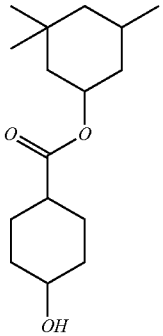

I-25

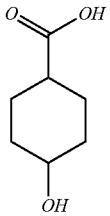

I-26

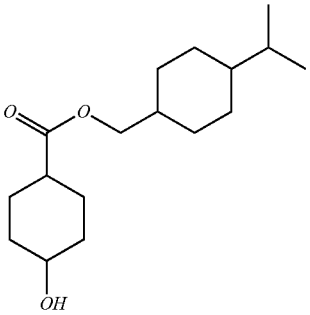

I-27

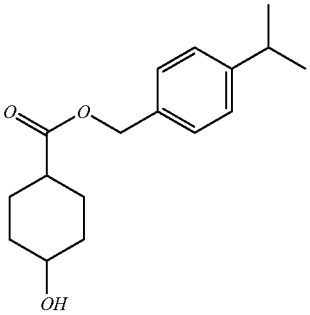

-continued

I-28

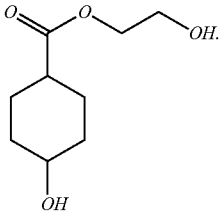

*14. The method according to claim 13, wherein said compound of formula I is a compound of formula I-20.*

*15. The method according to claim 8, wherein an effective amount of at least one compound of the formula I is administered to said subject.*

*16. The method according to claim 15, wherein the radicals R1, R2, R3, R4 and R5 stand, independently of one another, for H or OH, where 1, 2 or 3 of the radicals R1, R2, R3, R4 and R5 stand for OH.*

*17. The method according to claim 16, wherein said compound of formula I is a compound of formula Ia or Ib:*

Ia

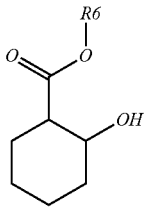

Ib

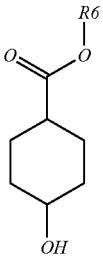

*in which R6 stands for*

*H,*

*$(CH_2—CH_2—O)_n—CH_2—CH_2—OH$, where n=0 to 20,*

*straight-chain or branched alkyl group having 1 to 20 C atoms,*

*straight-chain or branched alkenyl or alkynyl group having 2 to 20 C atoms and one or more double or triple bonds,*

*wherein the alkyl, alkenyl and alkynyl groups each optionally contain one or more saturated or unsaturated $C_3$- to $C_{12}$-cycloalkyl groups.*

*18. The method according to claim 17, wherein the R6 stands for*

*H,*

*$CH_2—CH_2—OH$,*

*straight-chain or branched alkyl group having 1 to 10 C atoms, which optionally contains a saturated or unsaturated $C_6$-cycloalkyl group.*

*19. The method according to claim 18, wherein the compound of the formula I is a compound selected from formulae I-15 to I-28*

I-15
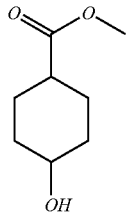
I-16
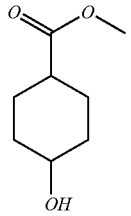
I-17
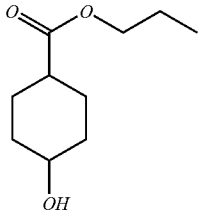
I-18
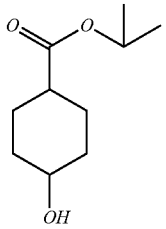
I-19
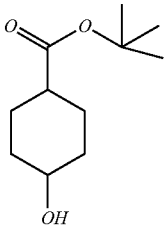
I-20
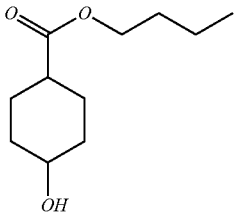
I-21
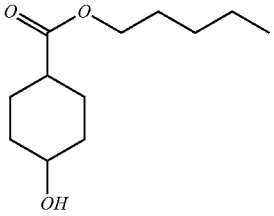
*-continued*
I-22
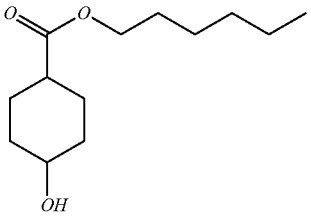
I-23
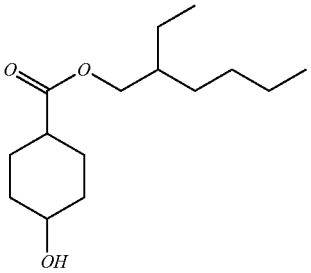
I-24
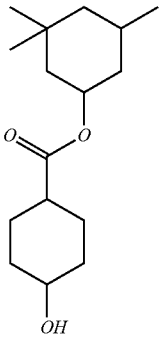
I-25
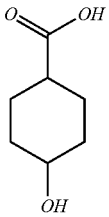
I-26
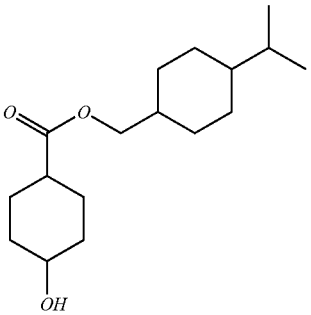

*-continued*
*I-27*
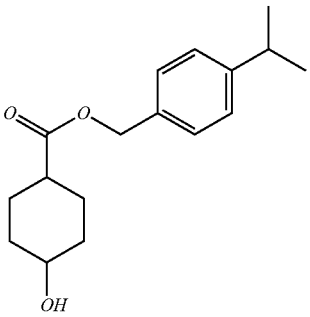
*I-28*
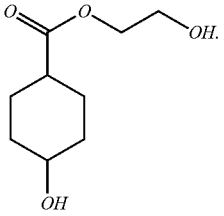
*20. The method according to claim 18, wherein said compound of formula I is a compound of formula I-20.*
* * * * *